US012747247B2

(12) United States Patent
Tsumura et al.

(10) Patent No.: US 12,747,247 B2
(45) Date of Patent: Sep. 29, 2026

(54) METHOD FOR PRODUCING BENZOXAZOLE DERIVATIVE HAVING BICYCLIC PIPERAZINE RING OR SALT THEREOF, AND METHOD FOR PRODUCING MATERIAL THEREOF

(71) Applicant: MEIJI SEIKA PHARMA CO., LTD., Tokyo (JP)

(72) Inventors: Takeshi Tsumura, Odawara (JP); Satoshi Isshiki, Tokyo (JP); Masayuki Okue, Odawara (JP); Toshiro Sasaki, Odawara (JP); Kenichi Fushihara, Odawara (JP); Shinsuke Mouri, Odawara (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 357 days.

(21) Appl. No.: 18/575,158

(22) PCT Filed: Jun. 30, 2022

(86) PCT No.: PCT/JP2022/026168
§ 371 (c)(1),
(2) Date: Dec. 28, 2023

(87) PCT Pub. No.: WO2023/277120
PCT Pub. Date: Jan. 5, 2023

(65) Prior Publication Data

US 2024/0309010 A1 Sep. 19, 2024

(30) Foreign Application Priority Data

Jun. 30, 2021 (JP) ................................ 2021-108230

(51) Int. Cl.
*C07D 487/08* (2006.01)

(52) U.S. Cl.
CPC ................................ *C07D 487/08* (2013.01)

(58) Field of Classification Search
CPC .. C07D 487/08; C07D 263/58; C07D 417/04; A61K 31/4995
See application file for complete search history.

(56) References Cited

U.S. PATENT DOCUMENTS

2019/0322686 A1* 10/2019 Tamura .................. A61P 35/00

FOREIGN PATENT DOCUMENTS

WO 2015/005429 A1 1/2015
WO 2018/124060 A1 7/2018

(Continued)

OTHER PUBLICATIONS

International Search Report for PCT/JP2022/026168 dated Sep. 13, 2022.

(Continued)

*Primary Examiner* — Kamal A Saeed
*Assistant Examiner* — Meghan C Heasley
(74) *Attorney, Agent, or Firm* — Sughrue Mion, PLLC

(57) ABSTRACT

A method for producing a compound represented by formula (1):

(1)

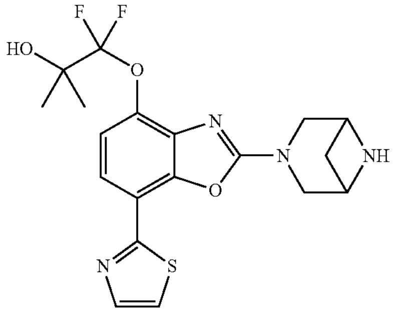

or a salt thereof, comprising:

a step B of producing a compound represented by formula (3):

(3)

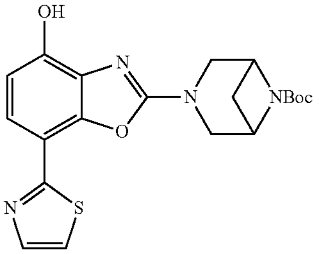

[in the formula (3), Boc represents a tert-butoxycarbonyl group]

or a salt thereof by using a compound represented by formula (2):

(2)

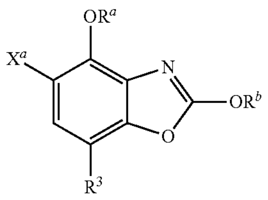

[in the formula (2), $R^a$ represents a hydrogen atom or an optionally substituted arylmethyl group, (Continued)

$R^b$ represents an optionally substituted alkyl or cyclic alkyl group, $R^3$ represents a hydrogen atom, a halogen atom, or a thiazol-2-yl group, and $X^a$ represents a hydrogen atom or a halogen atom] or a salt thereof; and a step C of producing the compound represented by the formula (1) or the salt thereof by using the compound represented by the formula (3) or the salt thereof.

11 Claims, No Drawings

(56) References Cited

FOREIGN PATENT DOCUMENTS

| | | |
|---|---|---|
| WO | 2020/004518 A1 | 1/2020 |
| WO | 2020/004521 A1 | 1/2020 |

OTHER PUBLICATIONS

International Preliminary Report on Patentability dated Jan. 11, 2024 with a Translation of the Written Opinion of the International Searching Authority in Application No. PCT/JP2022/026168.

* cited by examiner

METHOD FOR PRODUCING BENZOXAZOLE DERIVATIVE HAVING BICYCLIC PIPERAZINE RING OR SALT THEREOF, AND METHOD FOR PRODUCING MATERIAL THEREOF

This Application is a National Stage of International Application No. PCT/JP2022/026168 filed Jun. 30, 2022, claiming priority based on Japanese Patent Application No. 2021-108230 filed Jun. 30, 2021.

TECHNICAL FIELD

The present invention relates to a method for producing a benzoxazole derivative having a bicyclic piperazine ring or a salt thereof, and to a method for producing a material thereof. More specifically, the present invention relates to a method for producing 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol or a salt thereof, and to a method for producing a material thereof, namely, a 2-alkoxybenzo[d]oxazole derivative or a salt thereof.

BACKGROUND ART

1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol (a compound represented by formula (1) described later), which is a benzoxazole derivative having a bicyclic piperazine ring, has an excellent phosphodiesterase type (PDE4) selective inhibition activity (International Publication No. WO2018/124060).

1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol and salts thereof are known to be produced, for example, by obtaining an intermediate product: tert-butyl 3-(4-hydroxy-7-(thiazol-2-yl)benzo[d]oxazol-2-yl)-3,6-diazabicyclo[3.1.1]heptane-6-carboxylate (the compound represented by formula (3) described later) from 4-(benzyloxy)-7-bromobenzo[d]oxazole-2-thiol through an imination reaction, a cross-coupling reaction, a deprotection reaction (de-O-benzylation), and the like, and further subjecting the intermediate product to functional group conversion, a deprotection reaction, and the like (WO 2018/124060 A).

Meanwhile, 4-(benzyloxy)-7-bromobenzo[d]oxazole-2-thiol used in the above-described production method is known to be produced, for example, from 2-nitroresorcinol through five steps: a di-O-benzyl etherification reaction (formation of a protective group), a partial deprotection reaction (partial de-O-benzylation), a bromination reaction, a reduction reaction, and a cyclization reaction involving a leaving group (thiol group) (WO 2018/124060 A).

CITATION LIST

Patent Literature

[PTL 1] International Publication No. WO2018/124060

SUMMARY OF INVENTION

Technical Problem

In the already-existing production method using 4-(benzyloxy)-7-bromobenzo[d]oxazole-2-thiol, the production of 4-(benzyloxy)-7-bromobenzo[d]oxazole-2-thiol and the production of the above-described intermediate product using the same seem to include steps having room for improvement, such as (i) the use of benzyl bromide, which is lachrymatory and toxic, for the formation of a protective group, (ii) the use of boron trichloride, which is highly toxic, for the formation of the protective group, (iii) the use of carbon disulfide, which is highly toxic and is categorized as a special inflammable material under the Japanese Fire Service Act, for the cyclization reaction involving a thiol group, and also generation of hydrogen sulfide, which is highly poisonous, during the reaction, (iv) generation of hydrogen sulfide, which is highly poisonous, upon the substitution at the position of a thiol group with an imino group during the cyclization reaction involving the thiol group, and the like. Hence, this production method has problems of the use of highly toxic reagents, the high-risk handling operation, and the like.

The present invention has been made in view of the above-described problems, and an object of the present invention is to provide a novel method for producing 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol or a salt thereof, the method being better in safety and handleability and being suitable for industrial production.

Solution to Problem

To achieve the above-described object, the present inventors have conducted an intensive study, and consequently have found the use of 2-alkoxybenzo[d]oxazole derivative represented by formula (2) shown below or a salt thereof as a material of 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol or a salt thereof. Specifically, the compound represented by formula (2) and salts thereof can be produced by a method which does not require a reagent that is highly toxic and difficult to handle or a high-risk operation and further which does not involve generation of a toxic substance during the reaction.

Moreover, the production of a production intermediate, tert-butyl 3-(4-hydroxy-7-(thiazol-2-yl)benzo[d]oxazol-2-yl)-3,6-diazabicyclo[3.1.1]heptane-6-carboxylate or a salt thereof using the same and the production of 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol or a salt thereof using the same do not require a reagent that is highly toxic and difficult to handle or a high-risk operation, either. The present inventors have also found that the method for producing a compound represented by formula (2) or a salt thereof makes it possible to reduce the number of steps in comparison with the already-existing production method, and also makes it possible to obtain 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol or a salt thereof in a high percentage yield comparable to that of the already-existing production method.

Accordingly, the present inventors have found that the use of the compound represented by formula (2) or a salt thereof makes it possible to provide a novel industrial production method that is extremely excellent in safety and handleability, and this finding has led to the completion of the present invention. Specifically, the present invention provides inventions shown below.

[1] A method for producing a compound represented by formula (1):

(1)

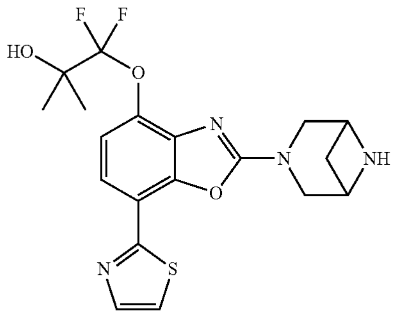

or a salt thereof, comprising:

a step B of producing a compound represented by formula (3):

(3)

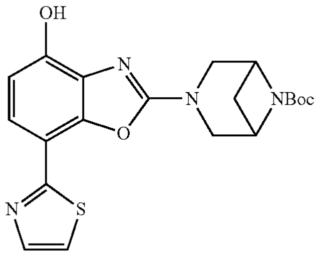

[in the formula (3), Boc represents a tert-butoxycarbonyl group]

or a salt thereof by using a compound represented by formula (2):

(2)

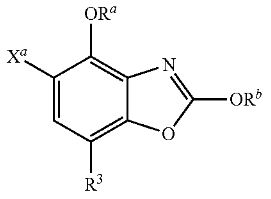

[in the formula (2), $R^a$ represents a hydrogen atom or an optionally substituted arylmethyl group, $R^b$ represents an optionally substituted alkyl or cyclic alkyl group, $R^3$ represents a hydrogen atom, a halogen atom, or a thiazol-2-yl group, and $X^a$ represents a hydrogen atom or a halogen atom] or a salt thereof; and a step C of producing a compound represented by formula (1) or a salt thereof by using the compound represented by the formula (3) or the salt thereof.

[2] The production method according to [1], wherein the step B is a step of substituting $OR^b$ of a compound (2-1) represented by the formula (2), where $R^a$ is optionally substituted arylmethyl group, $R^b$ is an optionally substituted alkyl group, $R^3$ is a halogen atom, and $X^a$ is a hydrogen atom, with tert-butyl 3,6-diazabicyclo[3.1.1]heptane-6-carboxylate, to produce a compound represented by formula (4):

(4)

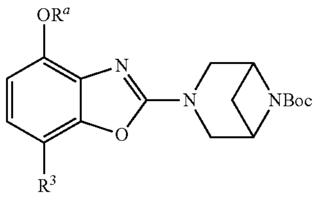

[in the formula (4), $R^a$ is an optionally substituted arylmethyl group, $R^3$ is a halogen atom, and Boc is a tert-butoxycarbonyl group], introducing a thiazol-2-yl group to the compound represented by the formula (4) by a cross-coupling reaction in the presence of a metal catalyst, to produce a compound represented by formula (5):

(5)

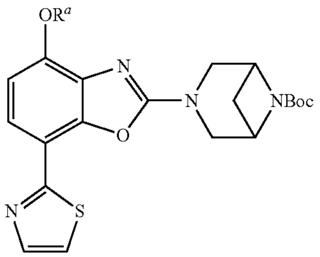

[in the formula (5), $R^a$ is an optionally substituted arylmethyl group, and Boc is a tert-butoxycarbonyl group], and reacting the compound represented by the formula (5) with an organic acid, to produce the compound represented by the formula (3) or the salt thereof.

[3] The production method according to [1], wherein the step B is a step of introducing a thiazol-2-yl group to a compound (2-1) represented by the formula (2), where $R^a$ is an optionally substituted arylmethyl group, $R^b$ is an optionally substituted alkyl group, $R^3$ is a halogen atom, and $X^a$ is a hydrogen atom, by a cross-coupling reaction in the presence of a metal catalyst, to produce a compound (2-11) represented by the formula (2), where $R^a$ is an optionally substituted arylmethyl group, $R^b$ is an optionally substituted alkyl group, $R^3$ is a thiazol-2-yl group, and $X^a$ is a hydrogen atom, substituting $OR^b$ of the compound (2-11) with tert-butyl 3,6-diazabicyclo[3.1.1]heptane-6-carboxylate, to produce a compound represented by formula (5):

(5)

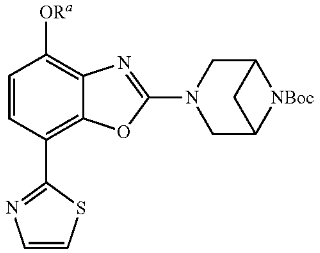

[in the formula (5), $R^a$ is an optionally substituted arylmethyl group, and Boc is a tert-butoxycarbonyl group], and reacting the compound represented by the formula (5) with an organic acid, to produce the compound represented by the formula (3) or the salt thereof.

[4] The production method according to [1], wherein the step B is a step of reacting a compound (2-2) represented by the formula (2), where $R^a$ is a hydrogen atom, $R^b$ is an optionally substituted alkyl group, $R^3$ is a hydrogen atom, and $X^a$ is a hydrogen atom, with a brominating agent, to produce a compound (2-21) represented by the formula (2), where $R^a$ is a hydrogen atom, $R^b$ is an optionally substituted alkyl group, $R^3$ is a bromine atom, and $X^a$ is a bromine atom, substituting $OR^b$ of the compound (2-21) with tert-butyl 3,6-diazabicyclo[3.1.1]heptane-6-carboxylate, to produce a compound represented by formula (8):

(8)

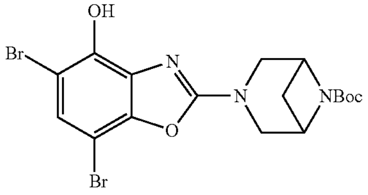

[in the formula (8), Boc is a tert-butoxycarbonyl group], introducing a thiazol-2-yl group to the compound represented by the formula (8) by a cross-coupling reaction in the presence of a metal catalyst, to produce a compound represented by formula (9):

(9)

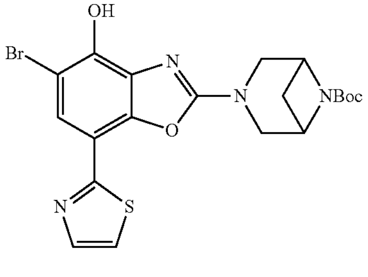

[in the formula (9), Boc is a tert-butoxycarbonyl group], and reacting the compound represented by the formula (9) with a metal, to produce the compound represented by the formula (3) or the salt thereof.

[5]

The production method according to any one of [1] to [4], comprising a step A of producing the compound represented by the formula (2) or the salt thereof by using a compound represented by formula (10):

(10)

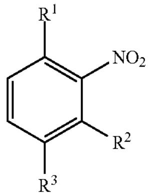

[in the formula (10), $R^1$ represents a hydroxy group or a halogen atom or an arylmethyloxy group, $R^2$ represents a hydroxy group or a halogen atom, $R^3$ represents a hydrogen atom, a halogen atom, or a thiazol-2-yl group] or a salt thereof.

[6] The production method according to [5], wherein the step A is a step of reacting a compound (10-1) represented by the formula (10), where $R^1$ is a halogen atom, $R^2$ is a halogen atom, and $R^3$ is a hydrogen atom, with benzyl alcohol, to produce a compound represented by formula (10-11):

(10-11)

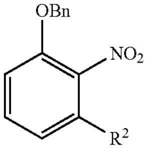

[in the formula (10-11), $R^2$ is a halogen atom, and Bn is a benzyl group], reacting the compound represented by the formula (10-11) with a brominating agent, to produce a compound represented by formula (10-12);

(10-12)

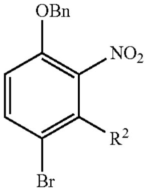

[in the formula (10-12), $R^2$ is a halogen atom, and Bn is a benzyl group], reacting the compound represented by the formula (10-12) with an aqueous alkaline solution, to produce a compound represented by formula (10-13);

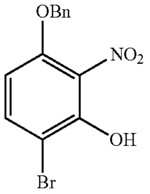

(10-13)

[in the formula (10-13), Bn is a benzyl group], reacting the compound represented by the formula (10-13) with a reducing agent, to produce a compound represented by formula (14):

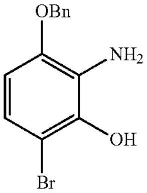

(14)

[in the formula (14), Bn is a benzyl group], and reacting the compound represented by the formula (14) with a tetraalkoxymethane in the presence of an acid catalyst, to produce the compound represented by the formula (2) or the salt thereof.

[7]

The production method according to [5], wherein the step A is a step of reducing a compound (10-2) represented by the formula (10), where $R^1$ is a hydroxy group, $R^2$ is a hydroxy group, and $R^3$ is a hydrogen atom, followed by a reaction with a tetraalkoxymethane in the presence of an acid catalyst and then by a reaction with a brominating agent, to produce the compound represented by the formula (2) or the salt thereof.

[8]

A compound represented by formula (15):

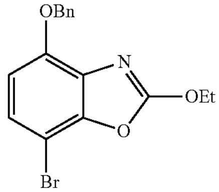

(15)

[in the formula (15), Bn is a benzyl group, and Et is an ethyl group]

or a salt thereof.

[9] A compound represented by formula (6);

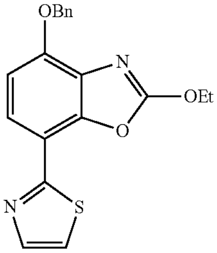

(6)

[in the formula (6), Bn is a benzyl group, and Et is an ethyl group]

or a salt thereof.

[10] A compound represented by formula (7);

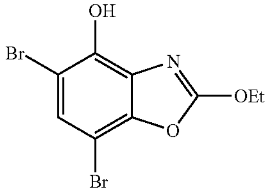

(7)

[in the formula (7), Et is an ethyl group] or a salt thereof.

[11] A compound represented by formula (8):

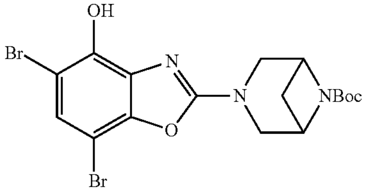

(8)

[in the formula (8), Boc is a tert-butoxycarbonyl group] or a salt thereof.

Advantageous Effects of Invention

According to the present invention, it is possible to provide a novel method for producing 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol (the compound represented by formula (1)) or a salt thereof, the method being excellent in safety and handleability and being suitable for industrial production. Moreover, according to the present invention, it is also possible to provide a 2-alkoxybenzo[d]oxazole derivative (a compound represented by formula (2)) or a salt thereof as a material preferably usable in the above-described production method, and a production method thereof.

DESCRIPTION OF EMBODIMENTS

Hereinafter, a method for producing a compound represented by formula (1) or a salt thereof and a method for producing a compound represented by formula (2) or a salt thereof used in the method for producing a compound represented by formula (1) of the present invention will be described in detail based on examples; however, the present invention is not limited to the range of the presented specific examples.

The method for producing a compound represented by formula (1) of the present invention comprises: a step B of producing a compound represented by formula (3) or a salt thereof by using a compound represented by formula (2) or a salt thereof, and a step C of producing a compound represented by formula (1) or a salt thereof by using the compound represented by formula (3) or the salt thereof (hereinafter, this method is simply referred to as "production method of the present invention" in some cases).

The compound obtained by the production method of the present invention is 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol represented by the following formula (1):

(1)

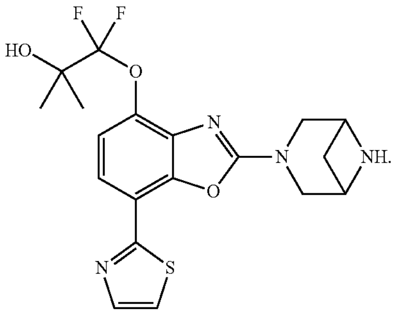

This compound has an excellent (type 4 PDE4 phosphodiesterase) inhibition activity, and is also excellent in metabolic stability (WO 2018/124060 A).

The compound obtained by the production method of the present invention may be a salt of the compound represented by formula (1) according to the present invention (hereinafter, referred to as "compound (1)" in some cases), and the salt is preferably a pharmacological acceptable salt. The pharmacologically acceptable salt is preferably in the form of an acid addition salt, and examples of acids for the acid addition salt include hydrohalic acids such as hydrofluoric acid, hydrochloric acid, hydrobromic acid, and hydroiodic acid; inorganic acids such as sulfuric acid, nitric acid, phosphoric acid, perhydroxic acid, and carbonic acid; organic carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid; acidic amino acids such as aspartic acid and glutamic acid; alkyl sulfonic acids such as methanesulfonic acid; and arylsulfonic acids such as p-toluenesulfonic acid.

The compound (1) and salts thereof can be obtained by using tert-butyl 3-(4-hydroxy-7-(thiazol-2-yl)benzo[d]oxazol-2-yl)-3,6-diazabicyclo[3.1.1]heptane-6-carboxylate (hereinafter, referred to as "compound (3)" in some cases) represented by the following formula (3):

(3)

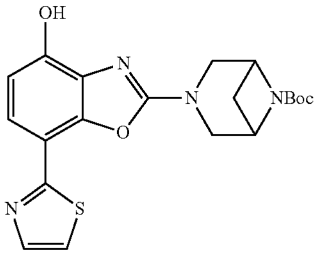

[in the formula (3), Boc represents a tert-butoxycarbonyl group]

or a salt thereof. As a method for obtaining the compound (1) from the compound (3), a known method or a method similar to a known method can be employed, as appropriate, and, for example, a method described in wo 2018/124060 A can be used. Salts of the compound (3), including preferred forms thereof, are the same as those described for the salts of the compound (1).

In the production method of the present invention, the compound (3) or a salt thereof is obtained by using a compound represented by formula (2) according to the present invention (hereinafter, referred to as "compound (2)" in some cases) or a salt thereof (step B). The compound (2) is a compound represented by the following formula (2):

(2)

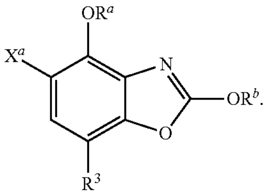

In the formula (2), $R^a$ represents a hydrogen atom or an optionally substituted arylmethyl group, $R^b$ represents an optionally substituted alkyl or cyclic alkyl group, $R^3$ represents a hydrogen atom, a halogen atom, or a thiazol-2-yl group, and $X^a$ represents a hydrogen atom or a halogen atom.

In this description, examples of "arylmethyl group" include a phenylmethyl group (benzyl group), a diphenylmethyl group (benzhydryl group), a triphenylmethyl group (trityl group), and the like, and a benzyl group is particularly preferable. The arylmethyl group represented by $R^a$ according to the present invention is optionally substituted with one substituent or two or more substituents which may be the same or different from each other.

In this description, an "arylmethyloxy group" is a group represented by the following formula: —OA, where A represents an arylmethyl group. Examples of the arylmethyl group include the groups described above, and a benzyl group is particularly preferable. The arylmethyloxy group represented by $R^1$ described below according to the present invention may be such that the arylmethyl group is optionally substituted with one substituent or two or more substituents which may be the same or different from each other.

In this description, an "alkyl group" refers to a linear or branched alkyl group, and the number of carbon atoms is preferably 1 to 6, and the number of carbon atoms is more preferably 1 to 3. The alkyl group represented by $R^b$ according to the present invention is optionally substituted with one substituent or two or more substituents which may be the same or different from each other. Examples of the alkyl group include a methyl group, an ethyl group, a n-propyl group, an isopropyl group, a n-butyl group, a sec-butyl group, an isobutyl group, a tert-butyl group, a n-pentyl group, a n-hexyl group, and the like.

In this description, a “cyclic alkyl group” refers to a ring-shaped alkyl group, and the number of carbon atoms, i.e., the number of ring members is preferably 3 to 8, and more preferably 3 to 6. The cyclic alkyl group represented by $R^b$ according to the present invention is optionally substituted with one substituent or two or more substituents which may be the same or different from each other. Examples of the cyclic alkyl group include a cyclopropyl group, a cyclobutyl group, a cyclopentyl group, a cyclohexyl group, a cycloheptyl group, a cyclooctyl group, and the like.

In this description, a “halogen atom” refers to a fluorine atom, a chlorine atom, a bromine atom, or an iodine atom.

Moreover, in this description, “optionally substituted” indicates that any one or two or more hydrogen atoms each may be substituted with an atom other than hydrogen or a group (substituent). When two or more hydrogen atoms are substituted, the substituents (atoms, groups) may be the same or different from each other. Examples of such substituents include a halogen atom, a cyano group, a nitro group, a hydroxy group, an amino group, a carbonyl group, a carboxy group, alkyl groups, alkoxy groups, cyclic alkoxy groups, alkylamino groups, cyclic alkylamino groups, an azide group, and the like.

Examples of the compound (2) according to the present invention include the following compounds: 2-methoxybenzo[d]oxazol-4-ol, 2-ethoxybenzo[d]oxazol-4-ol, 2-propoxybenzo[d]oxazol-4-ol, 2-isopropoxybenzo[d]oxazol-4-ol, 2-butoxybenzo[d]oxazol-4-ol, 2-isobutoxybenzo[d]oxazol-4-ol, 2-(sec-butoxy)benzo[d]oxazol-4-ol, 2-(tert-butoxy)benzo[d]oxazol-4-ol, 2-pentoxybenzo[d]oxazol-4-ol, 2-(pentan-2-yloxy)benzo[d]oxazol-4-ol, 2-[(3-methylbutan-2-yl)oxy]benzo[d]oxazol-4-ol, 2-(tert-pentyloxy)benzo[d]oxazol-4-ol, 2-(hexyloxy)benzo[d]oxazol-4-ol, 2-cyclopropoxybenzo[d]oxazol-4-ol, 2-cyclobutoxybenzo[d]oxazol-4-ol, 2-(cyclopentyloxy)benzo[d]oxazol-4-ol, 2-(cyclohexyloxy)benzo[d]oxazol-4-ol, 2-benzyloxybenzo[d]oxazol-4-ol, 5,7-dibromo-2-methoxybenzo[d]oxazol-4-ol, 5,7-dibromo-2-ethoxybenzo[d]oxazol-4-ol, 5,7-dibromo-2-propoxybenzo[d]oxazol-4-ol, 5,7-dibromo-2-butoxybenzo[d]oxazol-4-ol, 5,7-dibromo-2-isobutoxybenzo[d]oxazol-4-ol, 5,7-dibromo-2-(sec-butoxy)benzo[d]oxazol-4-ol, 5,7-dibromo-2-(tert-butoxy)benzo[d]oxazol-4-ol, 5,7-dibromo-2-pentoxybenzo[d]oxazol-4-ol, 5,7-dibromo-2-(pentan-2-yloxy)benzo[d]oxazol-4-ol, 5,7-dibromo-2-[(3-methylbutan-2-yl)oxy]benzo[d]oxazol-4-ol, 5,7-dibromo-2-(tert-pentyloxy)benzo[d]oxazol-4-ol, 5,7-dibromo-2-(hexyloxy)benzo[d]oxazol-4-ol, 5,7-dibromo-2-cyclopropoxybenzo[d]oxazol-4-ol, 5,7-dibromo-2-cyclobutoxybenzo[d]oxazol-4-ol, 5,7-dibromo-2-cyclobutoxybenzo[d]oxazol-4-ol, 5,7-dibromo-2-(cyclopentyloxy)benzo[d]oxazol-4-ol, 5,7-dibromo-2-(cyclohexyloxy)benzo[d]oxazol-4-ol, 5,7-dibromo-2-benzyloxybenzo[d]oxazol-4-ol, 4-(benzyloxy)-7-bromo-2-methoxybenzo[d]oxazole, 4-(benzyloxy)-7-bromo-2-ethoxybenzo[d]oxazole, 4-(benzyloxy)-7-bromo-2-propoxybenzo[d]oxazole, 4-(benzyloxy)-7-bromo-2-isopropoxybenzo[d]oxazole, 4-(benzyloxy)-7-bromo-2-butoxybenzo[d]oxazole, 4-(benzyloxy)-7-bromo-2-isobutoxybenzo[d]oxazole, 4-(benzyloxy)-7-bromo-2-4-(benzyloxy)-7-bromo-2-(sec-butoxy)benzo[d]oxazole, (tert-butoxy)benzo[d]oxazole, 4-(benzyloxy)-7-bromo-2-pentoxybenzo[d]oxazole, 4-(benzyloxy)-7-bromo-2-(pentan-2-yloxy)benzo[d]oxazole, 4-(benzyloxy)-7-bromo-2-[(3-methylbutan-2-yl)oxy]benzo[d]oxazole, 4-(benzyloxy)-7-bromo-2-(tert-pentyloxy)benzo[d]oxazole, 4-(benzyloxy)-7-bromo-2-(hexyloxy)benzo[d]oxazole, 4-(benzyloxy)-7-bromo-2-cyclopropoxybenzo[d]oxazole, 4-(benzyloxy)-7-bromo-2-cyclobutoxybenzo[d]oxazole, 4-(benzyloxy)-7-bromo-2-(cyclopentyloxy)benzo[d]oxazole, 4-(benzyloxy)-7-bromo-2-(cyclohexyloxy)benzo[d]oxazole, 2,4-di(benzyloxy)-7-bromobenzo[d]oxazole, 4-(benzyloxy)-2-methoxy-7-(thiazol-2-yl)benzo[d]oxazole, 4-(benzyloxy)-2-ethoxy-7-(thiazol-2-yl)benzo[d]oxazole, 4-(benzyloxy)-2-propoxy-7-(thiazol-2-yl)benzo[d]oxazole, 4-(benzyloxy)-2-isopropoxy-7-(thiazol-2-yl)benzo[d]oxazole, 4-(benzyloxy)-2-butoxy-7-(thiazol-2-yl)benzo[d]oxazole, 4-(benzyloxy)-2-isobutoxy-7-(thiazol-2-yl)benzo[d]oxazole, 4-(benzyloxy)-2-(sec-butoxy)-7-(thiazol-2-yl)benzo[d]oxazole, 4-(benzyloxy)-2-(tert-butoxy)-7-(thiazol-2-yl)benzo[d]oxazole, 4-(benzyloxy)-2-pentoxy-7-(thiazol-2-yl)benzo[d]oxazole, 4-(benzyloxy)-2-(pentan-2-yloxy)-7-(thiazol-2-yl)benzo[d]oxazole, 4-(benzyloxy)-2-[(3-methylbutan-2-yl)oxy]-7-(thiazol-2-yl)benzo[d]oxazole, 4-(benzyloxy)-2-(tert-pentyloxy)-7-(thiazol-2-yl)benzo[d]oxazole, 4-(benzyloxy)-2-(hexyloxy)-7-(thiazol-2-yl)benzo[d]oxazole, 4-(benzyloxy)-2-cyclopropoxy-7-(thiazol-2-yl)benzo[d]oxazole, 4-(benzyloxy)-2-cyclobutoxy-7-(thiazol-2-yl)benzo[d]oxazole, 4-(benzyloxy)-2-(cyclopentyloxy)-7-(thiazol-2-yl)benzo[d]oxazole, 4-(benzyloxy)-2-(cyclohexyloxy)-7-(thiazol-2-yl)benzo[d]oxazole, and 2,4-di(benzyloxy)-7-(thiazol-2-yl)benzo[d]oxazole; however, the present invention is not limited to these specific examples.

Of these examples, preferred as the compound (2) according to the present invention are 2-ethoxybenzo[d]oxazol-4-ol, 5,7-dibromo-2-ethoxybenzo[d]oxazol-4-ol represented by the following formula (7):

(7)

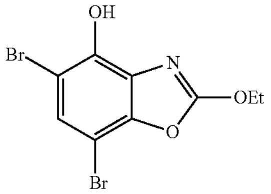

[in the formula (7), Et is an ethyl group], 4-(benzyloxy)-7-bromo-2-ethoxybenzo[d]oxazole represented by the following formula (15):

(15)

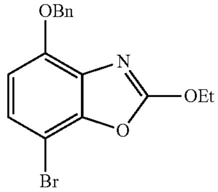

[in the formula (15), Bn is a benzyl group, and Et is an ethyl group], and 4-(benzyloxy)-2-ethoxy-7-(thiazol-2-yl)benzo[d]oxazole represented by the following formula (6):

(6)

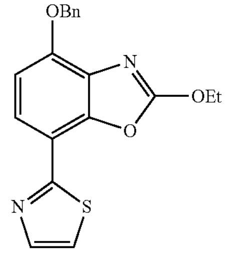

[in the formula (6), Bn is a benzyl group, and Et is an ethyl group].

Salts of the compound (2) according to the present invention, including preferred forms thereof, are the same as those described for the salts of the compound (1).

The compound (2) or a salt thereof according to the present invention is preferably obtained by a step A of producing the compound (2) or the salt thereof by using a compound represented by formula (10) shown below (hereinafter, referred to as "compound (10)" in some cases) or a salt thereof.

The compound (1) or a salt thereof according to the present invention can be produced by a representative method shown in scheme 1 below.

Scheme 1

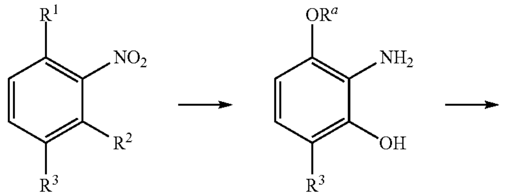

(10) A

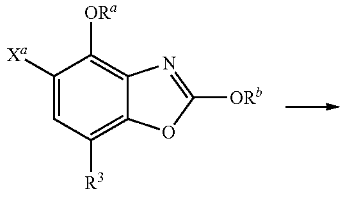

(2)

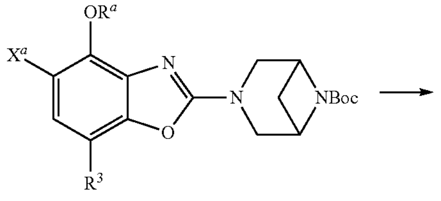

B

-continued

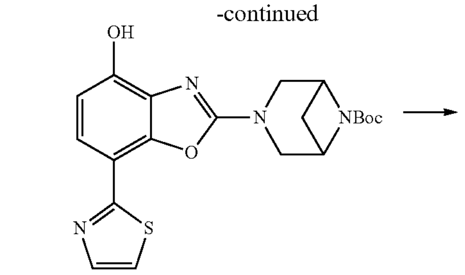

(3)

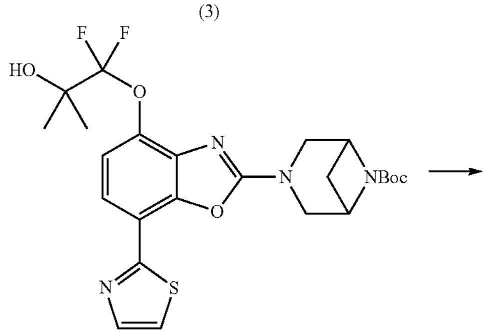

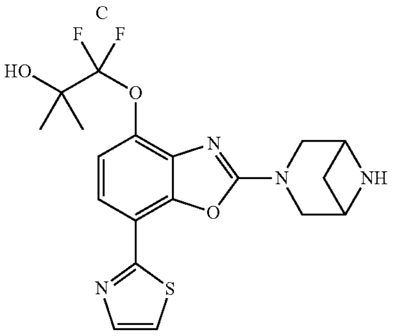

(1)

In each of the formulae in scheme 1 above, $R^1$ represents a hydroxy group or a halogen atom or an arylmethyloxy group, $R^2$ represents a hydroxy group or a halogen atom, $R^a$s each independently represents a hydrogen atom or an optionally substituted arylmethyl group, $R^b$ represents an optionally substituted alkyl or cyclic alkyl group, R's each independently represents a hydrogen atom, a halogen atom, or a thiazol-2-yl group, and $X^a$s each independently represents a hydrogen atom or a halogen atom.

In scheme 1 above, first, as a preferred mode of step A, the nitro group of the compound represented by formula (10) is reduced by a reduction reaction, to produce a compound represented by formula A (hereinafter, referred to as "compound A" in some cases), and then the compound (2) is obtained by a cyclization reaction of the compound A.

Subsequently, in scheme 1, as a preferred mode of the step B, the 2-alkoxy group ($OR^b$) of the obtained compound (2) is substituted with tert-butyl 3,6-diazabicyclo[3.1.1]heptane-6-carboxylate (substitution reaction) to obtain a compound represented by formula B (hereinafter, referred to as "compound B" in some cases) or the compound (3). Moreover, the compound B is subjected to introduction of a thiazol-2-yl group by a cross-coupling reaction, removal of a protective group on $R^a$ by a deprotection reaction, and if $X^a$ is other than a hydrogen atom, conversion of $X^a$ to a hydrogen atom, as appropriate, to obtain the compound (3).

After that, as a preferred mode of the step C, a compound represented by formula C (hereinafter, referred to as "compound C" in some cases) is obtained through O-alkylation of the compound (3), and then the tert-butoxycarbonyl group (hereinafter, shown as "BOC" in some cases) is removed by a deprotection reaction to obtain the compound (1).

The production method of the present invention preferably comprises, as the step A, a step of producing a compound (2) or a salt thereof either from preferably a compound (10-1), in which $R^1$ and $R^2$ are a halogen atom, and $R^3$ is a hydrogen atom, more preferably 2,6-difluoronitrobenzene, in which $R^1$ and $R^2$ are a fluorine atoms, and $R^3$ is a hydrogen atom, as the compound (10), or from a compound (10-2), in which $R^1$ and $R^2$ are a hydroxy group, and $R^3$ is a hydrogen atom, i.e., 2-nitroresorcinol as the compound (10).

When the compound (10-1) or, more preferably, 2,6-difluoronitrobenzene is used as the compound (10), for example, the compound (10-1) (preferably, 2,6-difluoronitrobenzene) is first reacted with benzyl alcohol (partial substitution reaction), to produce a compound (compound (10-11)) represented by the following formula (10-11):

(10-11)

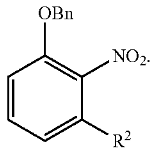

In the formula (10-11), Bn is a benzyl group (hereinafter, the same), and $R^2$ is a halogen atom. $R^2$ is more preferably a fluorine atom. Subsequently, the compound (10-11) is reacted with a brominating agent (bromination reaction), to produce a compound (compound (10-12)) represented by the following formula (10-12):

(10-12)

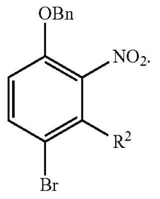

In the formula (10-12), $R^2$ is a halogen atom, and $R^2$ is more preferably a fluorine atom. Subsequently, the compound (10-12) is reacted with an aqueous alkaline solution (hydration reaction), to produce a compound (compound (10-13)) represented by the following formula (10-13):

(10-13)

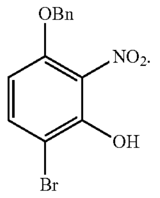

Moreover, the compound (10-13) is reacted with a reducing agent (reduction reaction) to obtain a compound (compound (14)) represented by the following formula (14):

(14)

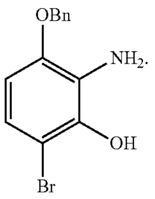

as the compound A. Subsequently, the compound (2) (for example, a compound represented by formula (15) described above) or a salt thereof can be produced by reacting the compound (14) with a tetraalkoxymethane (cyclization reaction involving an alkoxy group).

Meanwhile, when the compound (10-2) (2-nitroresorcinol) is used as the compound (10), for example, the compound (10-2) is first reacted with a reducing agent (reduction reaction), to produce the compound (10-21) (2-aminoresorcinol), and the compound (10-21) is reacted with a tetraalkoxymethane (cyclization reaction involving an alkoxy group), to produce the compound (10-22) (2-ethoxybenzo[d]oxazol-4-ol). Subsequently, a compound (2) (for example, a compound represented by formula (7) described above) or a salt thereof can be produced by reacting the compound (10-22) with a brominating agent (bromination reaction).

Moreover, the production method of the present invention preferably comprises, as the step B, a step of producing a compound (3) or a salt thereof either from preferably a compound (2-1), in which $R^a$ is an optionally substituted arylmethyl group, $R^b$ is an optionally substituted alkyl group, $R^3$ is a halogen atom, and $X^a$ is a hydrogen atom (more preferably, a compound in which $R^a$ is a benzyl group) as the compound (2), or from a compound (2-2), in which $R^a$ is a hydrogen atom, $R^b$ is an optionally substituted alkyl group, $R^3$ is a hydrogen atom, and $X^a$ is a hydrogen atom (more preferably, a compound in which $R^b$ is an ethyl group) as the compound (2).

When a compound (2-1) is used as the compound (2), for example, $OR^b$ of the compound (2-1) (more preferably, a compound in which $R^a$ is a benzyl group, and $R^3$ is a bromine atom) is first substituted with tert-butyl 3,6-diazabicyclo[3.1.1]heptane-6-carboxylate (substitution reaction), to produce a compound (compound (4), compound B) represented by the following formula (4):

(4)

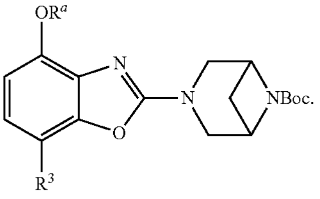

In the formula (4), $R^a$ is an optionally substituted arylmethyl group, and $R^3$ is a halogen atom. In formula (4), $R^a$ is preferably a benzyl group, and $R^3$ is preferably a bromine atom. Subsequently, a thiazol-2-yl group is introduced to the compound (4) by a cross-coupling reaction in the presence of a metal catalyst, to produce a compound (compound (5), compound B) represented by the following formula (5):

(5)

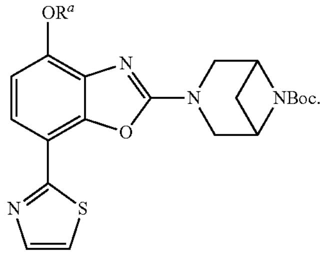

In the formula (5), $R^a$ is an optionally substituted arylmethyl group. In formula (5), $R^a$ is preferably a benzyl group. Subsequently, a compound (3) or a salt thereof can be produced by reacting the compound (5) with an organic acid (deprotection reaction).

Meanwhile, in another method in which a compound (2-1) is used as the compound (2), for example, a thiazol-2-yl group is first introduced to the compound (2-1) (more preferably, a compound in which $R^a$ is a benzyl group, and $R^b$ is an ethyl group) by a cross-coupling reaction in the presence of a metal catalyst, to produce a compound (2-11) represented by the formula (2), where $R^a$ is an optionally substituted arylmethyl group, $R^b$ is an optionally substituted alkyl group, $R^3$ is a thiazol-2-yl group, and $X^a$ is a hydrogen atom. The compound (2-11) is preferably a compound (compound (6)) represented by the following formula (6):

(6)

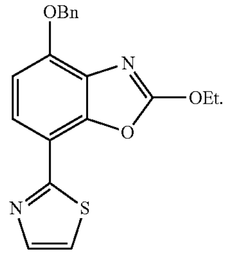

In the formula (6), Et is an ethyl group (hereinafter, the same). Subsequently, $OR^b$ of the compound (2-11) is substituted with tert-butyl 3,6-diazabicyclo[3.1.1]heptane-6-carboxylate (substitution reaction), to produce a compound (5) ($R^a$ is a benzyl group). Subsequently, a compound (3) or a salt thereof can be produced by reacting the compound (5) with an organic acid (deprotection reaction).

Moreover, when a compound (2-2) is used as the compound (2), for example, the compound (2-2) (more preferably a compound in which $R^b$ is an ethyl group) is first reacted with a brominating agent, to produce a compound (2-21) represented by the formula (2), where $R^a$ is a hydrogen atom, $R^b$ is an optionally substituted alkyl group, $R^3$ is a bromine atom, and $X^a$ is a bromine atom. The compound (2-21) is preferably a compound (compound (7)) represented by the following formula (7):

(7)

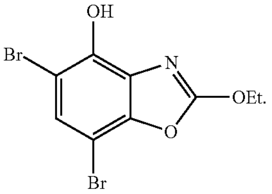

Subsequently, $OR^b$ of the compound (2-21) is substituted with tert-butyl 3,6-diazabicyclo[3.1.1]heptane-6-carboxylate (substitution reaction), to produce a compound (compound (8), compound B) represented by the following formula (8):

(8)

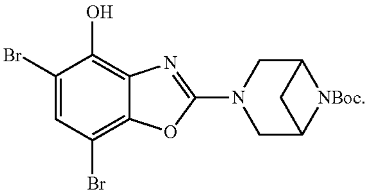

Subsequently, a thiazol-2-yl group is introduced to the compound (8) by a cross-coupling reaction in the presence of a metal catalyst, to produce a compound (compound (9), compound B) represented by the following formula (9):

(9)

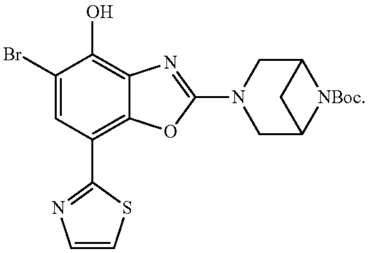

Subsequently, a compound (3) or a salt thereof can be produced by reacting the compound (9) with a metal (conversion reaction).

Each of the compounds serving as intermediates in the steps shown in scheme 1 described above may be isolated but is not necessarily isolated, and when the compound is not isolated, the reactions can be conducted successively.

Hereinafter, each reaction in scheme 1 will be described in further detail. Not that, in the following description, "equivalent" is chemical equivalent, and, for a functional group reacted in each reaction, the amount of molecules (the amount of substance) necessary for complete reaction of the functional group of the substrate in the reaction is designated as one equivalent.

(Partial Substitution Reaction)

In the production method of the present invention, preferably, the compound (10-1) is reacted with benzyl alcohol to obtain the compound (10-11) by a partial substitution reaction. The partial substitution reaction is preferably conducted by reacting a substrate (the compound (10-1) in this case) with benzyl alcohol in a suitable solvent in the presence or absence of a base, and preferred conditions for the reaction are shown below.

As the solvent, for example, it is possible to use one selected from hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, dichloromethane, chloroform, 1,2-dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of tetrahydrofuran, 2-methyltetrahydrofuran, 1,4-dioxane, acetonitrile, N,N-dimethylformamide, N,N-dimethylacetamide, dimethyl sulfoxide, and N-methyl-2-pyrrolidone, and, more preferably, may be at least one selected from the group consisting of N,N-dimethylformamide and dimethyl sulfoxide.

As the base, for example, it is possible to use one selected from salts such as sodium hydrogen carbonate, sodium carbonate, potassium hydrogen carbonate, potassium carbonate, cesium carbonate, sodium acetate, potassium acetate, sodium phosphate, potassium phosphate, lithium hydroxide, sodium hydroxide, potassium hydroxide, and barium hydroxide; amines such as trimethylamine, triethylamine, tributylamine, diisopropylethylamine, 2-(dimethylamino) ethanol, N-methylpyrrolidine, N-methylpiperidine, N-methylmorpholine, N,N'-dimethylpiperazine, N,N,N',N'-tetramethylethylenediamine, N,N-dimethylaniline, 1,4-diazabicyclo[2.2.2]octane, 1,5-diazabicyclo[4.3.0]non-5-ene, 1,8-diazabicyclo[5.4.0]undec-7-ene, pyridine, picoline, 4-(dimethylamino)pyridine, 2,6-lutidine, and 2,4,6-collidine; metal hydrides such as lithium hydride, sodium hydride, potassium hydride, barium hydride, and calcium hydride; metal alkoxides such as lithium methoxide, sodium methoxide, sodium ethoxide, sodium tert-butoxide, and potassium tert-butoxide; metal amides such as lithium amide, sodium amide, potassium amide, lithium diisopropylamide, lithium-2,2,6,6-tetramethylpiperidide, lithium bistrimethylsilylamide, sodium bistrimethylsilylamide, and potassium bistrimethylsilylamide; potassium trimethylsiloxide; and the like alone, or to use a mixture of two or more selected therefrom at an appropriate ratio.

Preferably, the base may be at least one selected from the group consisting of sodium carbonate, potassium carbonate, triethylamine, diisopropylethylamine, sodium tert-butoxide, and potassium tert-butoxide, and, more preferably, may be at least one selected from the group consisting of potassium carbonate and sodium tert-butoxide. The amount of the base used in the partial substitution reaction is 0.01 to 20 equivalents, preferably 0.1 to 10 equivalents, and more preferably 1 to 5 equivalents relative to the substrate.

The amount of benzyl alcohol used in the partial substitution reaction is 0.8 to 5 equivalents, and preferably 0.9 to 2 equivalents relative to the substrate.

The reaction temperature of the partial substitution reaction is in the range of 0 to 200° C., preferably in the range of 50 to 150° C., and more preferably in the range of 80 to 120° C.

The reaction time of the partial substitution reaction is in the range of 1 to 100 hours, preferably in the range of 5 to 50 hours, and more preferably in the range of 10 to 30 hours.

(Bromination Reaction)

In the production method of the present invention, preferably, the compound (2-2) is reacted with a brominating agent to obtain a compound (2-21) by a bromination reaction. In addition, the compound (10-11) is reacted with a brominating agent to obtain a compound (10-12) by a bromination reaction. Moreover, the compound (10-22) is reacted with a brominating agent to obtain a compound (2) by a bromination reaction. The bromination reaction is preferably conducted by reacting a substrate (the compound (2-2), the compound (10-11), or the compound (10-22) in these cases) with a brominating agent in a suitable solvent in the presence or absence of an acid catalyst, and preferred conditions therefor are shown below.

As the solvent, for example, it is possible to use one selected from protic solvents such as water, methanol, ethanol, n-propanol, 2-propanol, n-butanol, 2-butanol, and tert-butanol; hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, dichloromethane, chloroform, 1,2-dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of ethyl acetate, n-propyl acetate, isopropyl acetate, n-butyl acetate, acetonitrile, N,N-dimethylformamide, N,N-dimethylacetamide, and N-methyl-2-pyrrolidone, and, more preferably, may be at least one selected from the group consisting of acetonitrile and ethyl acetate.

Examples of the acid catalyst include organic acids such as formic acid, acetic acid, trifluoroacetic acid, propionic acid, lactic acid, succinic acid, citric acid, methanesulfonic acid, trifluoromethanesulfonic acid, 10-camphorsulfonic acid, benzenesulfonic acid, and p-toluenesulfonic acid; inorganic acids such as hydrochloric acid, hydrobromic acid, hydroiodic acid, sulfuric acid, nitric acid, phosphoric acid, perchloric acid, 12 molybdo(VI) phosphoric acid hydrate, and 12 tungsto(VI) phosphoric acid hydrate; Lewis acids such as tetrafluoroboric acid diethyl ether complex, boron trifluoride diethyl ether complex, boron trichloride, boron tribromide, magnesium chloride, magnesium bromide diethyl ether complex, zinc chloride, stannic chloride, ferric chloride, aluminum chloride, titanium tetrachloride, and zirconium tetrachloride; and the like. The examples also include chlorosilanes such as chlorotrimethylsilane, chlorotriethylsilane, chlorotriisopropylsilane, chloroisopropyldimethylsilane, chlorodiethylisopropylsilane, tert-butylchlorodimethylsilane, tert-butylchlorodiphenylsilane, tribenzylsilyl chloride, chlorotriphenylsilane, chloromethyldiphenylsilane, and di-tert-butylchloromethylsilane, and the like. One of these acid catalysts can be used alone, or a mixture of two or more acid catalysts selected therefrom may be used at an appropriate ratio.

Of these examples, preferably, the acid catalyst may be at least one (preferably, one) selected from the group consisting of acetic acid, tetrafluoroboric acid diethyl ether complex, and chlorotrimethylsilane, and, more preferably, may be at least one (preferably, one) selected from the group consisting of acetic acid and chlorotrimethylsilane, from the viewpoint of low toxicity.

The amount of the acid catalyst used in the bromination reaction is 0 to 1 equivalent, and preferably 0 to 0.7 equivalents relative to the substrate.

As the brominating agent, for example, it is possible to use one selected from bromine, bromine-1,4-dioxane complex, tetrabutylammonium tribromide, benzyltrimethylammonium tribromide, trimethylphenylammonium tribromide, 1-butyl-3-methylimidazolium tribromide, 1,8-diazabicyclo [5.4.0]-7-undecene hydrogen tribromide, pyridinium bromide perbromide, 4-dimethylaminopyridinium bromide perbromide, N-bromoacetamide, N-bromosuccinimide, N-bromophthalimide, N-bromosaccharin, dibromocyanuric acid, monosodium bromocyanurate, 1,3-dibromo-5,5-dimethylhydantoin, bromodimethylsulfonium bromide, bis(2,4,6-trimethylpyridine) bromonium hexafluorophosphate, bromotrimethylsilane, carbon tetrabromide, bromotrichloromethane, 1,2-dibromo-1,1,2,2-tetrachloroethane, 5,5-dibromomeldrum's acid, 2,4,4,6-tetrabromo-2,5-cyclohexadienone, boron tribromide, phosphorus tribromide, and the like alone, or to use a mixture of two or more selected therefrom at an appropriate ratio.

Preferably, the brominating agent may be at least one (preferably, one) selected from the group consisting of bromine, tetrabutylammonium tribromide, benzyltrimethylammonium tribromide, N-bromosuccinimide, N-bromosaccharin, and 1,3-dibromo-5,5-dimethylhydantoin, and, more preferably, may be at least one (preferably, one) selected from the group consisting of N-bromosuccinimide.

The amount of the brominating agent used in the bromination reaction is 0.8 to 5 equivalents, and preferably 1 to 2 equivalents relative to the substrate, when one bromine atom is introduced per molecule of the substrate. Meanwhile, when two bromine atoms are introduced per molecule of the substrate, the amount is 1.8 to 5 equivalents, and preferably 2 to 3 equivalents relative to the substrate.

The reaction temperature of the bromination reaction is in the range of −50 to 100° C., preferably in the range of −25 to 50° C., and more preferably in the range of −10 to 30° C.

The reaction time of the bromination reaction is in the range of 10 minutes to 12 hours, preferably in the range of 20 minutes to 6 hours, and more preferably in the range of 30 minutes to 4 hours.

(Hydration Reaction)

In the production method of the present invention, preferably, a compound (10-12) is reacted with an alkaline solution to obtain a compound (10-13) by a hydration reaction. The hydration is reaction preferably conducted by reacting a substrate (compound (10-12) in this case) in a suitable solvent with an aqueous alkaline solution, and preferred conditions therefor are shown below.

As the solvent, for example, it is possible to use one selected from hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, dichloromethane, chloroform, 1,2-dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of tetrahydrofuran, 2-methyltetrahydrofuran, 1,4-dioxane, acetonitrile, N,N-dimethylformamide, N,N-dimethylacetamide, dimethyl sulfoxide, and N-methyl-2-pyrrolidone, and, more preferably, may be at least one selected from the group consisting of N,N-dimethylacetamide and dimethyl sulfoxide.

As the aqueous alkaline solution, for example, it is possible to use one selected from aqueous solutions of sodium hydrogen carbonate, sodium carbonate, potassium hydrogen carbonate, potassium carbonate, cesium carbonate, sodium acetate, potassium acetate, sodium phosphate, lithium hydroxide, sodium hydroxide, potassium hydroxide, barium hydroxide, and the like alone, or to use a mixture of two or more selected therefrom at an appropriate ratio.

Preferably, the aqueous alkaline solution may be an aqueous solution of at least one (preferably, one) selected from the group consisting of sodium hydrogen carbonate, potassium carbonate, sodium hydroxide, and potassium hydroxide, and, more preferably, may be an aqueous solution of at least one (preferably, one) selected from the group consisting of sodium hydroxide and potassium hydroxide. In the hydration reaction, the concentration of the aqueous alkaline solution is not particularly limited, and can be adjusted, as appropriate.

The reaction temperature of the hydration reaction is in the range of 0 to 200° C., preferably in the range of 25 to 150° C., and more preferably in the range of 50 to 100° C.

The reaction time of the hydration reaction is in the range of 10 minutes to 20 hours, preferably in the range of 20 minutes to 10 hours, and more preferably in the range of 30 minutes to 5 hours.

(Reduction Reaction)

In the production method of the present invention, preferably, a compound (10-13) is reacted with a reducing agent to obtain a compound (14) by a reduction reaction. Meanwhile, a compound (10-2) is reacted with a reducing agent to obtain a compound (10-21) by a reduction reaction. The reduction reaction is preferably conducted by reacting a substrate (compound (10-13), compound (10-2) in these cases) with a reducing agent in a suitable solvent, and preferred conditions therefor are shown below.

As the solvent, for example, it is possible to use one selected from protic solvents such as water, methanol, ethanol, n-propanol, 2-propanol, n-butanol, 2-butanol, and tert-butanol; hydrocarbon-based solvents such as petroleum ether, n-pentane, n-hexane, n-heptane, cyclohexane, benzene, toluene, and xylene; halogen-containing solvents such as carbon tetrachloride, dichloromethane, chloroform, 1,2-dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propionate, n-butyl propyl propionate, isopropyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of water, methanol, ethanol, ethyl acetate, and n-butyl acetate, and, more preferably, may be at least one selected from the group consisting of water, ethanol, and ethyl acetate. Moreover, an acid such as formic acid, acetic acid, trifluoroacetic acid, hydrochloric acid, sulfuric acid, phosphoric acid, methanesulfonic acid, or toluenesulfonic acid, or a base such as sodium hydrogen carbonate, potassium hydrogen carbonate, sodium carbonate, potassium carbonate, cesium carbonate, lithium hydroxide, sodium hydroxide, or potassium hydroxide, may be added to the solvent as appropriate.

As the reducing agent, for example, it is possible to use one selected from metals such as zinc, aluminum, tin, stannous chloride, and iron; hydrogenation catalysts such as palladium, platinum, rhodium, and nickel, which are used with a hydrogen source and may be used with a support, as appropriate; inorganic salts such as sodium dithionite; and the like alone, or to use a mixture of two or more selected therefrom at an appropriate ratio.

Preferably, the reducing agent may be at least one (preferably, one) selected from the group consisting of zinc, iron, activated carbon-supported palladium, and sodium dithionite, and, more preferably, may be at least one (preferably, one) selected from the group consisting of activated carbon-supported palladium and sodium dithionite.

When the reducing agent is any of the above-described metals and/or the above-described inorganic salts in the reduction reaction, those are used in large excess, and the amount is (when both are contained, the total amount is) preferably 20 equivalents or less, and more preferably 10 equivalents or less relative to the substrate. When the reducing agent is any of the above-described hydrogenation catalysts, this is used in a catalytic amount, and the amount thereof is preferably 10% by weight or less, and more preferably 5% by weight or less relative to the total weight (wt) of inputted raw materials.

The reaction temperature of the reduction reaction is in the range of −10 to 100° C., preferably in the range of −5 to 80° C., and more preferably in the range of 0 to 50° C.

The reaction time of the reduction reaction is in the range of 10 minutes to 24 hours, preferably in the range of 20 minutes to 12 hours, and more preferably in the range of 30 minutes to 6 hours.

(Cyclization Reaction Involving Alkoxy Group)

In the production method of the present invention, preferably, a compound (14) is reacted with a tetraalkoxymethane to obtain a compound (2) by a cyclization reaction involving an alkoxy group. Moreover, a compound (10-21) is reacted with a tetraalkoxymethane to obtain a compound (10-22) by a cyclization reaction involving an alkoxy group.

The cyclization reaction involving an alkoxy group is preferably conducted by reacting a substrate (compound (14) or compound (10-21) in these cases) with a tetraalkoxymethane in a suitable solvent in the presence of an acid catalyst, and preferred conditions therefor are shown below.

As the solvent, for example, it is possible to use one selected from hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, chloroform, 1,2-dichloromethane, dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of n-hexane, n-heptane, toluene, xylene, methyl tert-butyl ether, 2-methyltetrahydrofuran, ethyl acetate, n-propyl acetate, isopropyl acetate, n-butyl acetate, isobutyl acetate, and tert-butyl acetate, and, more preferably, may be at least one selected from the group consisting of toluene and ethyl acetate.

As the acid catalyst, for example, it is possible to use one selected from organic acids such as formic acid, acetic acid, trifluoroacetic acid, propionic acid, lactic acid, succinic acid, citric acid, methanesulfonic acid, trifluoromethanesulfonic acid, 10-camphorsulfonic acid, benzenesulfonic acid, and p-toluenesulfonic acid; inorganic acids such as hydrochloric acid, hydrobromic acid, hydroiodic acid, sulfuric acid, nitric acid, phosphoric acid, and perchloric acid; Lewis acids such as boron trifluoride diethyl ether complex, boron trichloride, boron tribromide, magnesium chloride, magnesium bromide diethyl ether complex, zinc chloride, stannic chloride, ferric chloride, aluminum chloride, titanium tetrachloride, and zirconium tetrachloride; and the like alone, or to use a mixture of two or more selected therefrom at an appropriate ratio.

From the viewpoint of low toxicity, preferably, the acid catalyst may be at least one (preferably, one) selected from the group consisting of acetic acid and hydrochloric acid, and, more preferably, may be acetic acid.

The amount of the acid catalyst used in the cyclization reaction involving an alkoxy group is 0.01 to 1 equivalent, and preferably 0.1 to 0.6 equivalents relative to the substrate.

As the tetraalkoxymethane, for example, it is possible to use one selected from tetramethoxymethane, tetraethoxymethane, tetrapropoxymethane, tetrabutoxymethane, tetraisopropoxymethane, tetraisobutoxymethane, tetra(tert-butoxy)methane, tetra(sec-butoxy)methane, tetrapentoxymethane, tetra(pentan-2-yloxy)methane, tetra[(3-methylbutan-2-yl)oxy]methane, tetra(tert-pentyloxy)methane, tetracyclopropoxymethane, tetra(hexyloxy)methane, tetracyclobutoxymethane, tetra(cyclopentyloxy)methane, tetra (cyclohexyloxy)methane, and the like alone, or to use a mixture of two or more selected therefrom at an appropriate ratio.

Preferably, the tetraalkoxymethane may be at least one (preferably, one) selected from the group consisting of tetramethoxymethane, tetraethoxymethane, and tetrabenzyloxymethane, and, more preferably, may be tetraethoxymethane.

The amount of the tetraalkoxymethane used in the cyclization reaction involving an alkoxy group is 0.9 to 5 equivalents, and preferably 1 to 2 equivalents relative to the substrate.

The reaction temperature of the cyclization reaction involving an alkoxy group is in the range of 0 to 200° C., preferably in the range of 50 to 150° C., and more preferably in the range of 70 to 120° C.

The reaction time of the cyclization reaction involving an alkoxy group is in the range of 5 minutes to 10 hours, preferably in the range of 10 minutes to 5 hours, and more preferably in the range of 20 minutes to 3 hours.

(Substitution Reaction)

In the production method of the present invention, preferably, the 2-alkoxy group ($OR^b$) of a compound (2) (for example, compound (2-1), compound (2-11), or compound (2-21)) is substituted with tert-butyl 3,6-diazabicyclo[3.1.1]heptane-6-carboxylate to obtain a compound B (for example, compound (4), compound (5), compound (8)) by a substitution reaction. The substitution reaction is preferably conducted by reacting a substrate (compound (2) in this case) with tert-butyl 3,6-diazabicyclo[3.1.1]heptane-6-carboxylate in a suitable solvent in the presence or absence of an acid catalyst, and preferred conditions therefor are shown below.

As the acid catalyst, for example, it is possible to use one selected from organic acids such as formic acid, acetic acid, trifluoroacetic acid, propionic acid, lactic acid, succinic citric acid, acid, methanesulfonic acid, trifluoromethanesulfonic acid, 10-camphorsulfonic acid, benzenesulfonic acid, and p-toluenesulfonic acid; inorganic acids such as hydrochloric acid, hydrobromic acid, hydroiodic acid, sulfuric acid, nitric acid, phosphoric acid, and perchloric acid; Lewis acids such as boron trifluoride diethyl ether complex, boron trichloride, boron tribromide, zinc chloride, stannic chloride, ferric chloride, aluminum chloride, titanium tetrachloride, and zirconium tetrachloride; and the like alone, or to use a mixture of two or more selected therefrom at an appropriate ratio.

From the viewpoint of low toxicity, preferably, the acid catalyst may be at least one (preferably, one) selected from the group consisting of acetic acid and hydrochloric acid, and, more preferably, may be acetic acid.

The amount of the acid catalyst used in the substitution reaction is 0.01 to 1 equivalent, and preferably 0.1 to 0.6 equivalents relative to the substrate.

The amount of tert-butyl 3,6-diazabicyclo[3.1.1]heptane-6-carboxylate used in the substitution reaction is 0.9 to 3 equivalents, and preferably 1 to 1.5 equivalents relative to the substrate.

As the solvent, for example, it is possible to use one selected from hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, dichloromethane, chloroform, 1,2-dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of n-hexane, n-heptane, toluene, xylene, methyl tert-butyl ether, 2-methyltetrahydrofuran, ethyl acetate, n-propyl acetate, isopropyl acetate, n-butyl acetate, isobutyl acetate, and tert-butyl acetate, and, more preferably, may be at least one selected from the group consisting of toluene and ethyl acetate.

The reaction temperature of the substitution reaction is in the range of 0 to 200° C., preferably in the range of 30 to 150° C., and more preferably in the range of 60 to 130° C.

The reaction time of the substitution reaction is in the range of 10 minutes to 10 hours, preferably in the range of 20 minutes to 5 hours, and more preferably in the range of 30 minutes to 3 hours.

(Cross-Coupling Reaction)

When $R^3$ in the compound (2) or the compound B is other than a thiazol-2-yl group in the production method of the present invention, a thiazol-2-yl group is introduced to this position by a cross-coupling reaction, as appropriate. Preferably, a thiazol-2-yl group is introduced to position 7 of the compound (2) or the compound B (for example, compound (4), compound (2-1), compound (8)) by a cross-coupling reaction in the presence of a metal catalyst to obtain a compound B (for example, compound (5), compound (2-11), compound (9)) in which $R^3$ is a thiazol-2-yl group.

As the cross-coupling reaction, the Kumada-Tamao-Corriu coupling reaction, the Migita-Kosugi-Stille coupling reaction, the Suzuki-Miyaura coupling reaction, the Negishi coupling reaction, the Buchwald-Hartwig coupling reaction, the Hiyama coupling reaction, or the like can be used. Preferably, the Kumada-Tamao-Corriu coupling reaction, the Suzuki-Miyaura coupling reaction, or the Negishi coupling reaction can be used, and more preferably, the Negishi coupling reaction can be used.

The cross-coupling reaction is preferably conducted by reacting a substrate (compound (2) or compound B in these cases) with a 2-halothiazole (having been reacted with or not reacted with a reactant, as appropriate) in a suitable solvent in the presence of a metal catalyst, in the presence or absence of a ligand, and in the presence or absence of a base, and preferred conditions therefor are shown below.

As the solvent, for example, it is possible to use one selected from protic solvents such as water, methanol, ethanol, n-propanol, 2-propanol, n-butanol, 2-butanol, and tert-butanol; hydrocarbon-based solvents such as petroleum ether, n-pentane, n-hexane, n-heptane, cyclohexane, benzene, toluene, and xylene; aromatic hydrocarbon-based solvent such as benzene, toluene, and xylene; halogen-containing solvents such as carbon tetrachloride, dichloromethane, chloroform, 1,2-dichloroethane, chlorobenzene, and trifluoromethylbenzen; ether-based organic solvents such as diethyl ether, diisopropyl ether, methyl tert-butyl ether, methyl cyclopentyl ether, tetrahydrofuran, 2-methyltetrahydrofuran, 1,4-dioxane, 1,2-dimethoxyethane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, cyclohexanone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of water, ethanol, toluene, tetrahydrofuran, 1,4-dioxane, and N,N-dimethylformamide, and, more preferably, may be at least one selected from the group consisting of toluene, tetrahydrofuran, and N,N-dimethylformamide.

A “2-halothiazole” refers to a thiazole substituted with a halogen atom at position 2 thereof. The halogen atom may be a fluorine atom, a chlorine atom, a bromine atom, or an iodine atom, preferably a bromine atom or an iodine atom, and more preferably a bromine atom.

The reactant is for substituting a halogen atom of the 2-halothiazole with another reactive functional group, and may be one for carrying out a transmetallation reaction or the like. The reactant is preferably a combination of a catalyst described later used for the Miyaura-Ishiyama borylation reaction with a boron compound, such as pinacoldiborane, pinacolborane, or hypodiboric acid; a Grignard reagent; zinc dust; or the like, and is more preferably zinc dust or the like.

The amount of the 2-halothiazole used in the cross-coupling reaction is 1 to 20 equivalents, and preferably 1 to 10 equivalents relative to the substrate.

As the metal catalyst, for example, it is possible to use one selected from palladium metal, palladium(II) chloride, palladium(II) bromide, palladium(II) iodide, palladium(II) acetate, palladium(II) trifluoroacetate, palladium(II) propionate, palladium(II) pivalate, palladium(II) acetylacetonate, palladium(II) hexafluoroacetylacetonate, palladium(II) cyanide, palladium(II) sulfate, palladium(II) nitrate, palladium (II) oxide, palladium($\pi$-cinnamyl) chloride dimer, palladium (II) [1,3-bis(diphenylphosphino)propane]bis(benzonitrile) bis-tetrafluoroborate, trans-bis(diacetato)bis[o-(di-o-tolylphosphino)benzyl]dipalladium(II), bis(acetonitrile) dichloropalladium(II), trans-bis(dicyclohexylamino) palladium(II) acetate, bis[(dicyclohexyl)(4-dimethylaminophenyl)phosphine]dichloropalladium(II), [1,1'-bis(dicyclohexylphosphino)ferrocene]dichloropalladium(II), [1,2-bis(diphenylphosphino)ethane]dichloropalladium(II), [1,1'-bis(diphenylphosphino)ferrocene]dichloropalladium(II), [1,1'-bis(diphenylphosphino)ferrocene] dichloropalladium(II) dichloromethane[1,4-adduct, bis(diphenylphosphino)butane]dichloropalladium(II), [1,3-bis(diphenylphosphino)propane]dichloropalladium(II), bis[di-(tert-butyl)(4-trifluoromethylphenyl)phosphine] dichloropalladium(II), [1,1'-bis(di-tert-butylphosphino) ferrocene]dichloropalladium(II), bis(dibenzylideneacetone) palladium(0), bis(tricyclohexylphosphine)palladium(0), bis[tris-(2-methylphenyl)phosphine]palladium(0), bis(triphenylphosphine)dichloropalladium(II), bis(tri-tert-butylphosphine)palladium(0), bis[1,2-bis(diphenylphosphino)ethane]palladium(0), bis(benzonitrile) dichloropalladium(II), bis(benzonitrile)dibromopalladium (II), (2,2'-bipyridine)dichloropalladium(II), (2-butenyl) chloropalladium dimer, [1,3-bis(diphenylphosphino) propane]palladium(II) trifluoromethanesulfonate, [1,2-bis(phenylsulfinyl)ethane]palladium(II) acetate, diaceto bis(tricyclohexylphosphine)palladium(II), [2,2'-bis(diphenylphosphino)-1,1'-binaphthyl]dibromopalladium (II), [1,1'-bis(diphenylphosphino)ferrocene] dibromopalladium(II), (1,5-cyclooctadiene) dibromopalladium(II), [2,2'-bis(diphenylphosphino)-1,1'-binaphthyl]dichloropalladium(II), [1,1'-bis(diphenylphosphino)ferrocene]dichloropalladium(II) acetone adduct, bis(methyldiphenylphosphine)dichloropalladium(II), bis(triphenylphosphine)dichloropalladium(II), (1,10-phenanthroline)dichloropalladium(II), (N,N,N',N'-tetramethylethylenediamine)dichloropalladium(II), bis[di-tert-butyl (4-dimethylaminophenyl)phosphine]dichloropalladium(II), allylpalladium(II) chloride dimer, (ethylenediamine)palladium(II) chloride, chloro(1,5-cyclooctadiene)methylpalladium(II), (1,5-cyclooctadiene)dichloropalladium(II), bis(tricyclohexylphosphine)dichloropalladium(II), bis(tri-o-tolylphosphine)dichloropalladium (II), 2-(2'-di-tert-butylphosphine)biphenylpalladium(II) acetate, tetrakis(acetonitrile)palladium(II) tetrafluoroborate, tetrakis(triphenylphosphine)palladium(0), tris(dibenzylideneacetone) dipalladium(0), and tris(dibenzylideneacetone) dipalladium(0) chloroform adduct alone, or to use a mixture of two or more selected therefrom at an appropriate ratio.

Preferably, the metal catalyst may be at least one (preferably, one) selected from the group consisting of palladium (II) acetate, [1,1'-bis(diphenylphosphino)ferrocene]dichloropalladium(II) dichloromethane adduct, bis(triphenylphosphine)dichloropalladium(II), tetrakis(triphenylphosphine)palladium(0), tris(dibenzylideneacetone) dipalladium(0), and tris(dibenzylideneacetone) dipalladium(0) chloroform adduct, and, more preferably, may be at least one (preferably, one) selected from the group consisting of palladium(II) acetate and [1,1'-bis(diphenylphosphino)ferrocene]dichloropalladium(II) dichloromethane adduct.

As the ligand, for example, it is possible to use one selected from trimethylphosphine, triethylphosphine, tributylphosphine, tri-tert-butylphosphine, tri-tert-butylphosphonium tetrafluoroborate, trioctylphosphine, tricyclohexylphosphine, tricyclohexylphosphine tetrafluoroborate, tris(dimethylamino)phosphine, tris(diethylamino) phosphine, tris(3,5-dimethylphenyl)phosphine, tris(4-trifluoromethylphenyl)phosphine, tris(2,4,6-trimethylphenyl)phosphine, tris(2,4,6-trimethoxyphenyl) phosphine, tris(hydroxymethyl)phosphine, tris(4-fluorophenyl)phosphine, tris(pentafluorophenyl)phosphine, tris(o-methoxyphenyl)phosphine, tris(4-methoxyphenyl) phosphine, triphenylphosphine, triphenylphosphine oxide, tri(o-tolyl)phosphine, tri(o-tolyl)phosphine tetrafluoroborate, tri(m-tolyl)phosphine, tri(p-tolyl)phosphine, tri(2-furyl)phosphine, bis(dicyclohexylphosphinophenyl) ether, 1,1'-bis(diphenylphosphino)ferrocene, 1,1'-bis(di-tert-butylphosphino)ferrocene, bis[3,5-bis(trifluoromethyl)phenyl][2',6'-bis(isopropoxy)-3,6-dimethoxybiphenyl-2-yl] phosphine, 2,2'-bis(diphenylphosphino)-1,1'-biphenyl, 2,2'-bis(diphenylphosphino)-1,1'-binaphthyl, tri-1-naphthylphosphine, tris[3,5-bis(trifluoromethyl)phenyl] phosphine, tris(4-chlorophenyl)phosphine, 5-(di-tert-butylphosphino)-1',3',5'-triphenyl-1'H-[1,4]bipyrazole, 5-(di-tert-butylphosphino)-1-(naphthalen-1-yl)-1H-pyrazole, triallylphosphine, triisopropylphosphine, and triisopropylphosphonium tetrafluoroborate alone, or to use a mixture of two or more selected therefrom at an appropriate ratio.

Preferably, the ligand may be at least one (preferably, one) selected from the group consisting of triphenylphosphine, tri(o-tolyl)phosphine, tri(m-tolyl)phosphine, tri(p-tolyl)

phosphine, tri(2-furyl)phosphine, and 1,1'-bis(diphenylphosphino)ferrocene, and, more preferably, may be at least one (preferably, one) selected from the group consisting of tri(p-tolyl)phosphine and 1,1'-bis(diphenylphosphino) ferrocene.

The base, including preferred forms thereof, may be the same as those listed in the above-described (Partial Substitution Reaction).

The amount of the metal catalyst used in the cross-coupling reaction is 0.01 to 20% by mole, and preferably 0.1 to 15% by mole relative to the total amount in mole of inputted raw materials (excluding the solvent).

When the ligand and/or the base is used, the ratio between the metal catalyst and the ligand (metal catalyst:ligand) and the ratio between the metal catalyst and the base (metal catalyst:base) are each independently 1:0.25 to 20, and preferably 1:1 to 5, in terms of mole ratio.

The reaction temperature of the cross-coupling reaction is in the range of 0 to 200° C., preferably in the range of 30 to 150° C., and more preferably in the range of 60 to 120° C.

The reaction time of the cross-coupling reaction is in the range of 1 minute to 48 hours, preferably in the range of 15 minutes to 12 hours, and more preferably in the range of 30 minutes to 6 hours.

(Deprotection Reaction)

In the production method of the present invention, a hydrogenolysis reaction, a deprotection reaction using a Lewis acid, or a deprotection reaction using an organic acid or the like can be used as the deprotection reaction, and preferably a deprotection reaction using a Lewis acid and/or an organic acid can be used, and more preferably a deprotection reaction using an organic acid can be used.

In the production method of the present invention, when $R^a$ of the compound B has a protective group (for example, a benzyl group), this protective group is removed. Preferably, the protective group of $R^a$ is removed by reacting the compound B (for example, compound (5)) with an organic acid to obtain a compound (3). Meanwhile, Boc is removed by reacting the compound C with an organic acid to obtain a compound (1). The deprotection reaction preferably conducted by reacting a substrate (compound (5) or compound C in these cases) with an organic acid in a suitable solvent, and preferred conditions therefor are shown below.

As the solvent, for example, it is possible to use one selected from hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, dichloromethane, chloroform, 1,2-dichloroethane, and chlorobenzene; and ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether alone, or to use a mixture of two or more selected therefrom at an appropriate ratio.

Preferably, the solvent may be at least one selected from the group consisting of toluene, xylene, and dichloromethane, and, more preferably, may be at least one selected from the group consisting of toluene and dichloromethane.

As the organic acid, for example, it is possible to use one selected from trifluoroacetic acid, trichloroacetic acid, dichloroacetic acid, chloroacetic acid, methanesulfonic acid, trifluoromethanesulfonic acid, 10-camphorsulfonic acid, benzenesulfonic acid, and p-toluenesulfonic acid alone, or to use a mixture of two or more selected therefrom at an appropriate ratio. The organic acid may be preferably trifluoroacetic acid.

The amount of the organic acid used in the deprotection reaction is 1 to 50 equivalents, and preferably 5 to 20 equivalents relative to the substrate.

The reaction temperature of the deprotection reaction is in the range of 0 to 200° C., and preferably in the range of 20 to 150° C.

The reaction time of the deprotection reaction is in the range of 5 minutes to 48 hours, and preferably in the range of 20 minutes to 24 hours.

(Protection Reaction)

Note that, under conditions of scheme 1 described above, N-Boc, which is a protective group of the compound B, is also eliminated by the deprotection reaction on the compound B, and the free base form of the compound (3) is formed. For this reason, it is preferable to attach Boc again (to perform protection by substitution with Boc). In this case, after the free base form of the compound (3) is isolated, Boc can be attached again by an ordinary method known to those skilled in the art. Alternatively, this protection can be conducted by adjusting the reaction mixture to a neutral to basic condition after completion of the above-described deprotection reaction, and then reacting a substrate (the free base form of the compound (3) in this case) in the reaction mixture with di-tert-butyl dicarbonate in the presence or absence of a suitable auxiliary solvent. The latter method is preferable. Preferred conditions of the latter protection reaction are shown below.

As the auxiliary solvent, for example, it is possible to use one selected from protic solvents such as water, methanol, ethanol, n-propanol, 2-propanol, n-butanol, 2-butanol, and tert-butanol; hydrocarbon-based organic solvents such as petroleum ether, n-pentane, n-hexane, n-heptane, cyclohexane, benzene, toluene, and xylene; halogenated hydrocarbon-based organic solvents such as carbon tetrachloride, dichloromethane, chloroform, 1,2-dichloroethane, and chlorobenzene; ether-based organic solvents such as diethyl ether, diisopropyl ether, methyl tert-butyl ether, methyl cyclopentyl ether, tetrahydrofuran, 2-methyltetrahydrofuran, 1,4-dioxane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethyl sulfoxide, and N-methyl-2-pyrrolidone; and the like alone, or to use a mixture of two or more selected therefrom at an appropriate ratio.

Preferably, the solvent may be at least one selected from the group consisting of water, methanol, ethanol, n-propanol, 2-propanol, dichloromethane, chloroform, and ethyl acetate, and, more preferably, may be at least one selected from the group consisting of water, methanol, and dichloromethane.

To adjust the reaction mixture to a neutral to basic condition, for example, it is possible to use one selected from salts such as sodium hydrogen carbonate, sodium carbonate, potassium hydrogen carbonate, potassium carbonate, cesium carbonate, sodium acetate, potassium acetate, sodium phosphate, potassium phosphate, lithium hydroxide, sodium hydroxide, potassium hydroxide, and barium hydroxide; amines such as ammonia, methylamine, ethylamine, cyclohexylamine, ethanolamine, aniline, dimethylamine, diethylamine, dibutylamine, dicyclohexylamine, bistrimethylsilylamine, pyrrolidine, piperidine, piperazine, morpholine, trimethylamine, triethylamine, tributylamine, diisopropylethylamine, 2-(dimethylamino) ethanol, N-methylpyrrolidine, N-methylpiperidine, N-methylmorpholine, N,N'-dimethylpiperazine, N,N,N',N'-tetramethylethylenediamine, N,N-dimethylaniline, 1,4-diazabicyclo[2.2.2]octane, 1,5-diazabicyclo[4.3.0]non-5-ene, 1,8-diazabicyclo[5.4.0]undec-7-ene, pyridine, picoline, 4-(dimethylamino)pyridine, 2,6-lutidine, and 2,4,6-collidine; metal alkoxides such as lithium methoxide, sodium methoxide, sodium ethoxide, sodium tert-butoxide, and potassium tert-butoxide; organic acids such as formic acid, acetic acid, trifluoroacetic propionic acid, lactic acid, succinic acid, acid, citric acid, methanesulfonic acid, trifluoromethanesulfonic acid, 10-camphorsulfonic acid, benzenesulfonic acid, and p-toluenesulfonic acid; inorganic acids such as hydrochloric acid, hydrobromic acid, hydroiodic acid, sulfuric acid, nitric acid, phosphoric acid, and perchloric acid; Lewis acids such as boron trifluoride diethyl ether complex, boron trichloride, boron tribromide, magnesium chloride, magnesium bromide diethyl ether complex, zinc chloride, stannic chloride, ferric chloride, aluminum chloride, titanium tetrachloride, and zirconium tetrachloride; and the like alone, or to use a mixture of two or more selected therefrom at an appropriate ratio.

Of these examples, at least one (preferably, one) selected from the group consisting of sodium hydrogen carbonate, sodium carbonate, potassium hydrogen carbonate, potassium carbonate, sodium hydroxide, potassium hydroxide, acetic acid, trifluoroacetic acid, methanesulfonic acid, hydrochloric acid, sulfuric acid, nitric acid, and the like may be preferable, and at least one (preferably, one) selected from the group consisting of sodium hydrogen carbonate, sodium hydroxide, hydrochloric acid, and sulfuric acid may be more preferable, from the viewpoint of low toxicity. Here, the pH of the reaction mixture is adjusted to about 6.8 to 12.0, and preferably is adjusted to about 7.0 to 9.5.

Di-tert-butyl dicarbonate used is 0.9 to 5 equivalents, and preferably 1 to 2 equivalents relative to the substrate.

The reaction temperature of the protection reaction is in the range of 0 to 100° C., preferably in the range of 10 to 80° C., and more preferably in the range of 20 to 60° C.

The reaction time of the protection reaction is in the range of 10 minutes to 24 hours, preferably in the range of 20 minutes to 12 hours, and more preferably in the range of 30 minutes to 6 hours.

(Conversion Reaction)

As the conversion reaction of a halogen atom to a hydrogen atom in the production method of the present invention, a method can be used in which the halogen atom is eliminated by a transmetallation reaction, a reduction reaction, or the like, and preferably a reduction reaction by catalytic hydrogenation or with a metal can be used, and more preferably a reduction reaction with a metal can be used.

When $X^a$ of the compound B is not a hydrogen atom but a halogen atom in the production method of the present invention, the halogen atom is converted to a hydrogen atom. Preferably, the halogen atom of $X^a$ is converted to a hydrogen atom by reacting the compound B (for example, the compound (9)) with a metal to obtain the compound (3). The conversion reaction is preferably conducted by reacting a substrate (the compound B in this case) with a metal in a suitable solvent in the presence or absence of an acid or a base, and preferred conditions therefor are shown below.

As the solvent, for example, it is possible to use one selected from protic solvents such as water, methanol, ethanol, n-propanol, 2-propanol, n-butanol, 2-butanol, and tert-butanol; hydrocarbon-based solvents such as petroleum ether, n-pentane, n-hexane, n-heptane, cyclohexane, benzene, toluene, and xylene; aromatic hydrocarbon-based solvents such as benzene, toluene, and xylene; ether-based organic solvents such as diethyl ether, diisopropyl ether, methyl tert-butyl ether, methyl cyclopentyl ether, tetrahydrofuran, 2-methyltetrahydrofuran, 1,4-dioxane, 1,2-dimethoxyethane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; and aprotic polar solvents such as acetone, 2-butanone, methyl isobutyl ketone, cyclohexanone, acetonitrile, propionitrile, N,N-dimethylformamide, N,N-dimethylacetamide, dimethyl sulfoxide, and N-methyl-2-pyrrolidone alone, or to use a mixture of two or more selected therefrom at an appropriate ratio.

Preferably, the solvent may be at least one selected from the group consisting of water, methanol, ethanol, n-propanol, 2-propanol, tetrahydrofuran, and 1,4-dioxane, and, more preferably, may be at least one selected from the group consisting of water, 1,4-dioxane, and ethanol.

As the acid, for example, it is possible to use one selected from mineral acids such as hydrochloric acid, hydrobromic acid, hydroiodic acid, sulfuric acid, phosphoric acid, and nitric acid; carboxylic acids such as formic acid, acetic acid, propionic acid, and trifluoroacetic acid; ammonium salts of carboxylic acids such as ammonium carbonate, ammonium formate, and ammonium acetate; and the like alone, or to use a mixture of two or more selected therefrom at an appropriate ratio.

As the base, for example, it is possible to use one selected from salts such as sodium hydrogen carbonate, sodium carbonate, potassium hydrogen carbonate, potassium carbonate, cesium carbonate, sodium acetate, potassium acetate, sodium phosphate, potassium phosphate, lithium hydroxide, sodium hydroxide, potassium hydroxide, and barium hydroxide;

amines such as ammonia, methylamine, ethylamine, cyclohexylamine, ethanolamine, aniline, dimethylamine, diethylamine, dibutylamine, dicyclohexylamine, bistrimethylsilylamine, pyrrolidine, piperidine, piperazine, morpholine, trimethylamine, triethylamine, tributylamine, diisopropylethylamine, 2-(dimethylamino) ethanol, N-methylpyrrolidine, N-methylpiperidine, N-methylmorpholine, N,N'-dimethylpiperazine, N,N,N',N'-tetramethylethylenediamine, N,N-dimethylaniline, 1,4-diazabicyclo[2.2.2]octane, 1,5-diazabicyclo[4.3.0]non-5-ene, 1,8-diazabicyclo[5.4.0]undec-7-ene, pyridine, picoline, 4-(dimethylamino)pyridine, 2,6-lutidine, and 2,4,6-collidine; metal alkoxides such as lithium methoxide, sodium methoxide, sodium ethoxide, sodium tert-butoxide, and potassium tert-butoxide; and the like alone, or to use a mixture of two or more selected therefrom at an appropriate ratio.

Preferably, the base may be at least one selected from the group consisting of sodium hydroxide, potassium hydroxide, ammonium formate, or ammonium acetate, and, more preferably, may be at least one selected from the group consisting of sodium hydroxide or ammonium formate.

The amount of the acid or base used in the conversion reaction is 10 to 50 equivalents, preferably 20 to 40 equivalents, and more preferably 20 to 30 equivalents relative to the substrate.

As the metal, for example, it is possible to use one selected from samarium(II) iodide, ytterbium(III) iodide, aluminum, zinc, iron, tin, samarium, ytterbium, or the like alone, or to use a mixture of two or more selected therefrom at an appropriate ratio.

The metal may preferably be at least one (preferably, one) selected from the group consisting of zinc and iron, and, more preferably, may be zinc.

The amount of the metal used in the conversion reaction is 10 to 50 equivalents, preferably 20 to 40 equivalents, and more preferably 20 to 30 equivalents relative to the substrate.

The reaction temperature of the conversion reaction is in the range of 0 to 200° C., preferably in the range of 30 to 150° C., and more preferably in the range of 60 to 120° C.

The reaction time of the conversion reaction is in the range of 30 minutes to 24 hours, preferably in the range of 1 hours to 12 hours, and more preferably in the range of 2 hours to 6 hours.

(O-Alkylation Reaction)

In the production method of the present invention, preferably, the hydroxy group at position 4 of the compound (3) is dialkylated by an O-alkylation reaction to obtain a compound C. The O-alkylation reaction is preferably conducted by reacting a substrate (compound (3) in this case) with ethyl 2-bromo-2,2-difluoroacetate in a suitable solvent in the presence or absence of a base, followed by dialkylation with an organometallic reagent, and preferred conditions therefor are shown below.

As the solvent, for example, it is possible to use one selected from protic solvents such as water, methanol, ethanol, n-propanol, 2-propanol, n-butanol, 2-butanol, and tert-butanol; hydrocarbon-based solvents such as petroleum ether, n-pentane, n-hexane, n-heptane, cyclohexane, benzene, toluene, and xylene; ether-based organic solvents such as diethyl ether, diisopropyl ether, methyl tert-butyl ether, methyl cyclopentyl ether, tetrahydrofuran, 2-methyltetrahydrofuran, 1,4-dioxane, 1,2-dimethoxyethane, and diphenyl ether; ester-based organic solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, cyclohexanone, acetonitrile, propionitrile, N,N-dimethylformamide, N,N-dimethylacetamide, dimethyl sulfoxide, and N-methyl-2-pyrrolidone, and the like alone, or to use a mixture of two or more selected therefrom at an appropriate ratio.

Preferably, the solvent may be at least one selected from the group consisting of methanol, ethanol, toluene, tetrahydrofuran, ethyl acetate, acetonitrile, and N,N-dimethylformamide, and, more preferably, may be at least one selected from the group consisting of acetonitrile and N,N-dimethylformamide.

As the bases, for example, it is possible to use one selected from salts such as sodium hydrogen carbonate, sodium carbonate, potassium hydrogen carbonate, potassium carbonate, cesium carbonate, sodium acetate, potassium acetate, sodium phosphate, potassium phosphate, lithium hydroxide, sodium hydroxide, potassium hydroxide, and barium hydroxide; amines such as trimethylamine, triethylamine, tributylamine, diisopropylethylamine, 2-(dimethylamino) ethanol, N-methylpyrrolidine, N-methylpiperidine, N-methylmorpholine, N,N'-dimethylpiperazine, N,N,N',N'-tetramethylethylenediamine, N,N-dimethylaniline, 1,4-diazabicyclo[2.2.2]octane, 1,5-diazabicyclo[4.3.0]non-5-ene, 1,8-diazabicyclo[5.4.0]undec-7-ene, pyridine, picoline, 4-(dimethylamino)pyridine, 2,6-lutidine, and 2,4,6-collidine; metal hydrides such as lithium hydride, sodium hydride, potassium hydride, barium hydride, and calcium hydride; metal alkoxides such as lithium methoxide, sodium methoxide, sodium ethoxide, sodium tert-butoxide, and potassium tert-butoxide; metal amides such as lithium amide, sodium amide, potassium amide, lithium diisopropylamide, lithium-2,2,6,6-tetramethylpiperidide, lithium bistrimethylsilylamide, sodium bistrimethylsilylamide, and potassium bistrimethylsilylamide; potassium trimethylsiloxide; and the like alone, or to use a mixture of two or more selected therefrom at an appropriate ratio.

Preferably, the base may be at least one selected from the group consisting of sodium carbonate, potassium carbonate, triethylamine, 1,8-diazabicyclo[5.4.0]undec-7-ene, sodium hydride, and sodium tert-butoxide, and, more preferably, may be at least one selected from the group consisting of 1,8-diazabicyclo[5.4.0]undec-7-ene and sodium tert-butoxide.

The amount of the base used in the O-alkylation reaction (the reaction with ethyl 2-bromo-2,2-difluoroacetate) is 1 to 20 equivalents, and preferably 2 to 5 equivalents relative to the substrate.

The amount of ethyl 2-bromo-2,2-difluoroacetate used in the O-alkylation reaction is 1 to 10 equivalents, and preferably 2 to 6 equivalents relative to the substrate.

The reaction temperature of the o-alkylation reaction (the reaction with ethyl 2-bromo-2,2-difluoroacetate) is in the range of 0 to 100° C., preferably in the range of 10 to 60° C., and more preferably in the range of 15 to 40° C.

The reaction time of the O-alkylation reaction (the reaction with ethyl 2-bromo-2,2-difluoroacetate) is in the range of 5 minutes to 24 hours, preferably in the range of 10 minutes to 12 hours, and more preferably in the range of 20 minutes to 6 hours.

As the organometallic reagent, for example, it is possible to use one selected from organomagnesium reagents, organolithium reagents, organozinc reagents, organoboron reagents, organotin reagents, organosilicon reagents, organobismuth reagents, organogermanium reagents, organomercury reagents, and the like alone, or to use a mixture of two or more selected therefrom at an appropriate ratio.

The organometallic reagent may preferably be at least one (preferably, one) selected from the group consisting of organomagnesium reagents, organolithium reagents, and organozinc reagents, and more preferably may be an organomagnesium reagent.

The amount of the organometallic reagent used in the O-alkylation reaction is 2 to 10 equivalents, and preferably 2.5 to 5 equivalents relative to the substrate.

The reaction temperature of the O-alkylation reaction (the reaction with an organometallic reagent) is in the range of 0 to 100° C., preferably in the range of 10 to 60° C., and more preferably in the range of 15 to 40° C.

The reaction time of the O-alkylation reaction (the reaction with an organometallic reagent) is in the range of 5 minutes to 24 hours, preferably in the range of 10 minutes to 12 hours, and more preferably in the range of 20 minutes to 6 hours.

EXAMPLES

Hereinafter, the present invention will be described in further detail by way of Examples; however, the present invention is not limited to these Examples. Examples below may be subjected to various applications, alterations, modifications, and the like within a range not deviating from the scope of the present invention.

Abbreviations in Examples described below have the following meanings.

M: mol/L $^1$H-NMR: Results of a proton nuclear magnetic resonance spectrum of an obtained compound Pd—C: palladium catalyst supported on activated carbon THF: tetrahydrofuran DMF: N,N-dimethylformamide DMSO: dimethyl sulfoxide Boc: tert-butoxycarbonyl group $(Boc)_2O$: di-tert-butyl dicarbonate Bn: benzyl group.

Example 1

[Synthesis Example 1]
3-Benzyloxy-6-bromo-2-nitrophenol

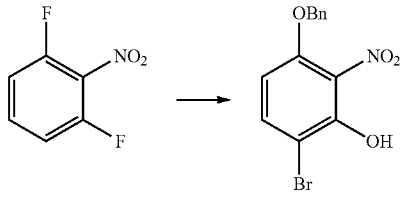 [SMILES: O=[N+]([O-])c1c(F)cccc1F ; O=[N+]([O-])c1c(OCc2ccccc2)ccc(Br)c1O]

2,6-Difluoronitrobenzene (52.75 g, 331.6 mmol) was dissolved in DMSO (158 mL), followed by addition of benzyl alcohol (35.86 g, 331.6 mmol) and potassium carbonate (91.65 g, 663 mmol) and by stirring at 90° C. for 24 hours, to obtain a reaction liquid containing a compound represented by the above-described formula (10-11), where $R^2$ is a fluorine atom. The reaction liquid was cooled, then diluted with ethyl acetate (422 mL), and washed with 211 mL of water and 211 mL of 0.1M hydrochloric acid successively. The obtained organic layer was concentrated, while the solvent was being replaced with acetonitrile, to obtain 211 mL of an acetonitrile solution. To the obtained solution, acetonitrile (211 mL), N-bromosuccinimide (88.53 g, 497.4 mmol), and acetic acid (4.75 mL, 83.1 mmol) were added, and cooled to 10° C. or below, followed by addition of chlorotrimethylsilane (18.02 g, 165.9 mmol) and by stirring at 10° C. or below for 2 hours, to obtain a reaction liquid containing a compound represented by the above-described formula (10-12), where $R^2$ is a fluorine atom. To the reaction liquid, water (164 mL) and a 20% aqueous sodium hydrogen sulfite solution (164 mL) were added followed by stirring, then toluene (528 mL) was added followed by stirring, and the aqueous layer was removed. The obtained organic layer was washed twice with a 2M aqueous sodium hydroxide solution (249 mL), and DMSO (492 mL) was added. The mixture was concentrated to evaporate toluene. To the obtained solution, a 6.25M aqueous sodium hydroxide solution (127 mL) was added, followed by stirring at 70° C. for 1 hour. The reaction liquid was cooled, and then toluene (1266 mL) were added followed by (633 mL) and water stirring. Then, the organic layer was removed. To the obtained aqueous layer, toluene (791 mL) and a 6M hydrochloric acid (146 mL) were added followed by stirring, and then the aqueous layer was removed. The obtained organic layer was washed with water, and then concentrated, while the solvent was being replaced with 2-propanol, to obtain a 2-propanol (370 mL) solution. A solid was precipitated by adding water (296 mL) to the solution followed by cooling and stirring. Then, the solid was separated, washed with a liquid mixture of 2-propanol/water=1/2, and dried to obtain 84.08 g of the title compound (Percentage yield: 78.2%).

$^1$H-NMR (400 MHZ, CDCl3) δ ppm: 9.81 (s, 1H), 7.61 (d, J=9.1 Hz, 1H), 7.45-7.32 (m, 5H), 6.55 (d, J=9.1 Hz, 1H), 5.20 (s, 2H).

[Synthesis Example 2]
2-Amino-3-benzyloxy-6-bromophenol

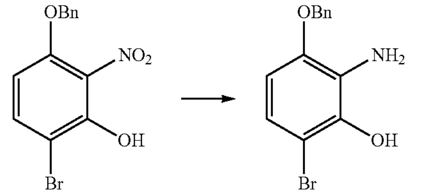 [SMILES: O=[N+]([O-])c1c(OCc2ccccc2)ccc(Br)c1O ; Nc1c(OCc2ccccc2)ccc(Br)c1O]

Sodium dithionite (Purity: 90.6%) (118.58 g, 617 mmol) was dissolved in water (480 mL) followed by cooling to 10° C. 3-Benzyloxy-6-bromo-2-nitrophenol (40.0 g, 123.4 mmol) obtained in Synthesis Example 1 was dissolved in ethanol (560 mL), and added to an aqueous sodium dithionite solution, followed by stirring at 3 to 10° C. for 1 hour. To the reaction liquid, water (1200 mL) was added followed by stirring. Then, the formed solid was collected by filtration, washed with water, and then dried to obtain 29.9 g of the title compound (Percentage yield: 82.4%).

$^1$H-NMR (400 MHZ, CDCl3) δ ppm: 7.45-7.33 (m, 5H), 6.80 (d, J=8.7 Hz, 1H), 6.44 (d, J=8.7 Hz, 1H), 5.37 (br s, 1H), 5.07 (s, 2H), 3.91 (br s, 2H).

[Synthesis Example 3] tert-Butyl 3-(4-Benzyloxy-7-bromobenzo[d]oxazol-2-yl)-3,6-diazabicyclo[3.1.1]heptane-6-carboxylate

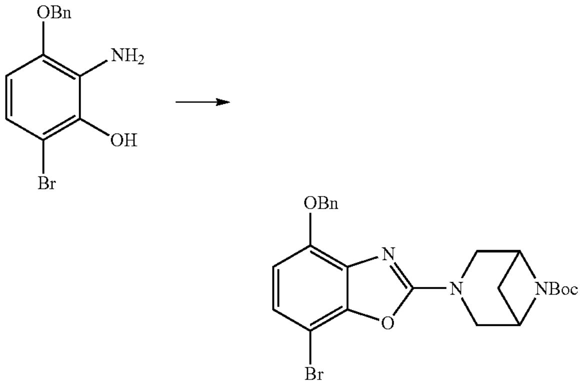

2-Amino-3-benzyloxy-6-bromophenol (10.0 g, 33.99 mmol) obtained in Synthesis Example 2 was suspended in toluene (20 mL), and acetic acid (0.98 mL, 17.1 mmol) and tetraethoxymethane (7.84 mL, 37.3 mmol) were added, followed by heating under reflux for 30 minutes to obtain a reaction liquid containing a compound represented by the formula (15). To the reaction liquid, tert-butyl 3,6-diazabicyclo[3.1.1]heptane-6-carboxylate (8.79 g, 44.3 mmol) and toluene (6 mL) were added, followed by heating under reflux for 2 hours. The reaction liquid was cooled, then diluted with toluene (40 mL), washed with a 5% aqueous sodium hydrogen carbonate solution (40 mL) and water (40 mL) successively, and then concentrated to 24 mL. To the obtained solution, n-heptane (180 mL) was added to precipitate a solid. After cooling and stirring, the solid was collected by filtration, washed with n-heptane, and dried to obtain 15.93 g of the title compound (Percentage yield: 93.7%).

$^1$H-NMR (400 MHZ, CDCl3) δ ppm: 7.44 (d, J=6.9 Hz, 2H), 7.37-7.25 (m, 3H), 6.97 (d, J=8.4 Hz, 1H), 6.59 (d, J=8.4 Hz, 1H), 5.35 (s, 2H), 4.35-4.20 (m, 4H), 3.76 (d, J=11.0 Hz, 2H), 2.75-2.67 (m, 1H), 1.55 (d, J=9.2 Hz, 1H), 1.41 (s, 9H).

[Synthesis Example 4] tert-Butyl 3-(4-Benzyloxy-7-(thiazol-2-yl)benzo[d]oxazol-2-yl)-3,6-diazabicyclo[3.1.1]heptane-6-carboxylate

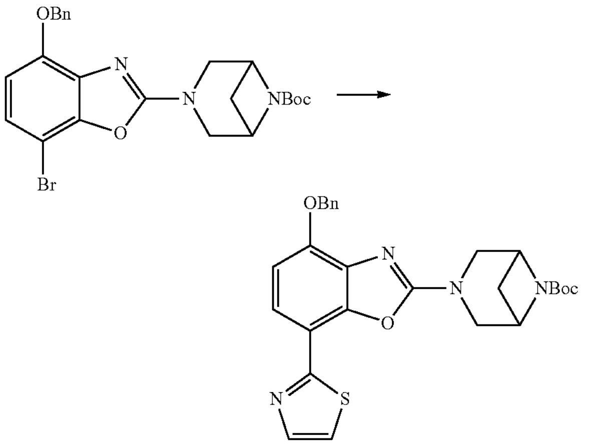

Zinc dust (6.47 g, 98.9 mmol) was suspended in DMF (22.5 mL) followed by addition of chlorotrimethylsilane (0.6 mL, 4.7 mmol) and by stirring at 60° C. for 1 hour. To the reaction liquid, 2-bromothiazole (6.7 mL, 75.6 mmol) was added, followed by stirring for 20 minutes. Then, a solution of tert-butyl 3-(4-benzyloxy-7-bromobenzo[d]oxazol-2-yl)-3,6-diazabicyclo[3.1.1]heptane-6-carboxylate (7.5 g, 15.0 mmol) obtained in Synthesis Example 3 in toluene (15 mL), copper (I) chloride (0.15 g, 1.5 mmol), and [1,1'-bis(diphenylphosphino)ferrocene]dichloropalladium(II) dichloromethane adduct (0.61 g, 0.75 mmol) were added, followed by stirring at 85° C. for 1 hour. The reaction liquid was cooled, and then toluene (225 mL) and 1M hydrochloric acid (225 mL) were added followed by stirring for 30 minutes. Then, insoluble matter was removed by filtration. The aqueous layer was removed, and the obtained organic layer was washed with water, and then concentrated. To the concentration residue, 2-propanol (75 mL) was added followed by stirring. The formed crystals were collected by filtration, and the obtained crystals were washed with 2-propanol, and then dried under reduced pressure to obtain 6.67 g of the title compound (Percentage yield: 88%).

$^1$H-NMR (400 MHZ, CDCl3) δ ppm: 7.88 (d, J=3.2 Hz, 1H), 7.75 (d, J=8.7 Hz, 1H), 7.48 (d, J=7.4 Hz, 2H), 7.38-7.25 (m, 4H), 6.80 (d, J=8.7 Hz, 1H), 5.44 (s, 2H), 4.45-4.25 (m, 4H), 3.83 (d, J=10.6 Hz, 2H), 2.75-2.68 (m, 1H), 1.58 (d, J=8.7 Hz, 1H), 1.42 (s, 9H).

[Synthesis Example 5] tert-Butyl 3-(4-Hydroxy-7-(thiazol-2-yl)benzo[d]oxazol-2-yl)-3,6-diazabicyclo[3.1.1]heptane-6-carboxylate

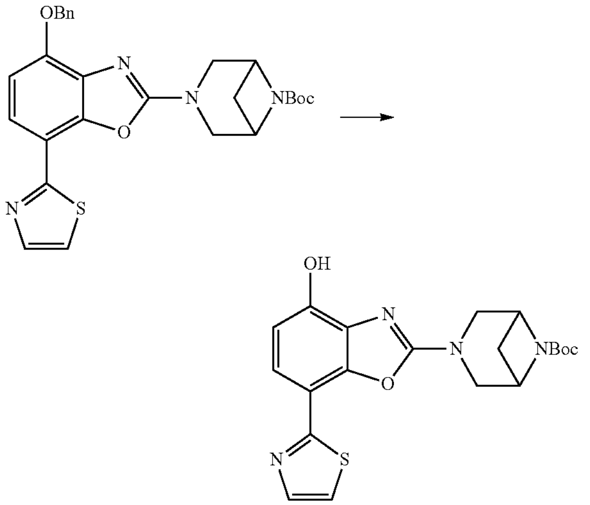

tert-Butyl 3-(4-benzyloxy-7-(thiazol-2-yl)benzo[d]oxazol-2-yl)-3,6-diazabicyclo[3.1.1]heptane-6-carboxylate (50.0 g, 99.09 mmol) obtained in Synthesis Example 4 was suspended in toluene (150 mL), followed by addition of trifluoroacetic acid (150 mL, 1960 mmol) and by stirring at 80° C. for 20 hours. The reaction liquid was cooled to about room temperature, and methanol (300 mL), water (200 mL), and dichloromethane (480 mL) cooled to about 5° C. in advance were added. Subsequently, a 5M aqueous sodium hydroxide solution (400 mL) was added, followed by stirring at room temperature, and the pH was adjusted to about 8.6 with 6M hydrochloric acid. (Boc) 20 (25.0 mL, 109.0 mmol) was added followed by heating to 30° C. After 20 minutes, a 5% aqueous sodium hydrogen carbonate solution (83.2 mL, 49.50 mmol) was added, and after 30 minutes, a 5% aqueous sodium hydrogen carbonate solution (83.2 mL, 49.50 mmol) was further added, followed by stirring for 1 hour. The aqueous layer and the organic layer of the reaction liquid were separated, and the aqueous layer was extracted again with dichloromethane (100 mL). The combined organic layers were concentrated under reduced pressure to approximately 250 mL, and then addition of acetonitrile (300 mL) and concentration under reduced pressure to approximately 250 mL were repeated twice. After crystallization and maturation at room temperature for 30 minutes and stirring at 60° C. for 1 hour, the temperature was lowered to room temperature over 1 hour for maturation, followed by further maturation on an ice bath for 1 hour. The formed solid was collected by filtration, washed with cooled acetonitrile (75 mL), and then through-flow dried. To the obtained crude title compound, acetonitrile (250 mL) was added, followed by stirring at 80° C. for 1 hour. The temperature was lowered to room temperature over 2 hours for maturation, followed by further maturation on an ice bath for 1 hour. The solid was collected by filtration, washed with cooled acetonitrile (75 mL), and then dried under reduced pressure at 40° C., to obtain 42.2 g of a monoacetonitrile solvate of the title compound (Percentage yield: 93.5%).

$^1$H-NMR (400 MHZ, CDCl3) δ ppm: 9.44 (br s, 1H), 7.90 (d, J=3.2 Hz, 1H), 7.81 (d, J=8.7 Hz, 1H), 7.38 (d, J=3.2 Hz, 1H), 6.87 (d, J=8.7 Hz, 1H), 4.38-4.18 (m, 4H), 3.80-3.68 (m, 2H), 2.75-2.67 (m, 1H), 1.55 (d, J=8.7 Hz, 1H), 1.37 (s, 9H).

[Synthesis Example 6] tert-Butyl 3-(4-(1,1-Difluoro-2-hydroxy-2-methylpropoxy)-7-(thiazol-2-yl)benzo[d]oxazol-2-yl)-3,6-diazabicyclo[3.1.1]heptane-6-carboxylate

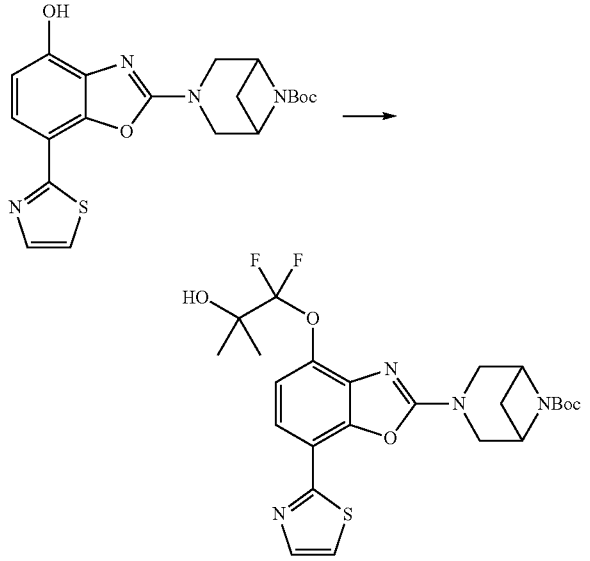

tert-Butyl 3-(4-hydroxy-7-(thiazol-2-yl)benzo[d]oxazol-2-yl)-3,6-diazabicyclo[3.1.1]heptane-6-carboxylate (50.0 g, 120.6 mmol) obtained in Synthesis Example 5 was dissolved in acetonitrile (225 mL), and ethyl 2-bromo-2,2-difluoroacetate (46.7 mL, 361.9 mmol) and 1,8-diazabicyclo[5.4.0]undec-7-ene (54.0 mL, 361.9 mmol) were added, followed by stirring at 30° C. for 3 hours. The reaction liquid was cooled to about 0° C., toluene (750 mL) and 0.3M hydrochloric acid cooled in advance were added followed by stirring, and the aqueous layer was removed. The obtained organic layer was washed twice with water (250 mL), and magnesium sulfate (5 g) was added followed by filtration. The filtrate was concentrated under reduced pressure to 250 mL, and after addition of toluene (250 mL), concentrated under reduced pressure to 250 mL. The obtained solution was cooled to 5° C., and a 1.08 M methylmagnesium bromide THF solution (336 mL, 361.9 mmol) was added, followed by stirring at room temperature for 2 hours. The reaction liquid was cooled to about 0° C., toluene (500 mL) and 1M hydrochloric acid (500 m) were added followed by stirring, and the aqueous layer was removed. The obtained organic layer was washed with a 0.1M aqueous sodium hydroxide solution (500 mL), a 10% aqueous potassium hydrogen sulfate solution (500 mL), and water (500 mL) successively, and then concentrated under reduced pressure to 250 mL. To the obtained solution, activated carbon (5 g) was added followed by stirring at 60° C. for 1 hour and by filtration through Celite. The filtrate was concentrated under reduced pressure to 250 mL followed by addition of ethanol (750 mL), and concentrated under reduced pressure to 250 mL followed by the same operation again. The obtained solution was stirred at room temperature for 2 hours, and then stirred at 0° C. for 1 hour to cause crystal precipitation. The formed crystals were collected by filtration, and washed with ethanol (100 mL). To the crystals, ethanol (500 mL) was added followed by heating to 70° C. and by stirring for 3 hours. Then, the temperature was lowered to room temperature over 2 hours followed by stirring overnight. The solution was cooled to 0° C. or below, and then stirred for 1 hour. The obtained crystals were washed with ethanol (2 vol) at 10° C. or below, and then dried under reduced pressure to obtain 50.69 g of a monoethanol solvate of the title compound (Percentage yield: 73.9%).

$^1$H-NMR (400 MHZ, DMSO-d6) δ ppm: 8.05 (s, J=4.0 Hz, 1H), 7.97 (s, J=4.0 Hz, 1H), 7.79 (s, J=10.0 Hz, 1H), 7.21 (s, J=10.0 Hz, 1H), 5.59 (s, 1H), 4.38-3.70 (m, 6H), 2.70-2.55 (m, 1H), 1.61 (d, J=8.0 Hz, 1H), 1.41 (s, 6H), 1.27 (S, 9H).

[Synthesis Example 7] 1-{[2-(3,6-Diazabicyclo[3.1.1]heptan-3-yl)-7-(1,3-thiazol-2-yl)-1,3-benzoxazol-4-yl]oxy}-1,1-difluoro-2-methylpropan-2-ol

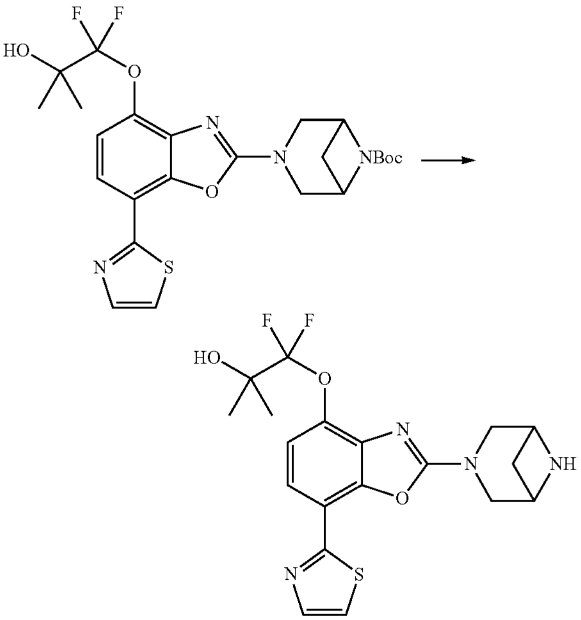

tert-Butyl 3-(4-(1,1-difluoro-2-hydroxy-2-methylpropoxy)-7-(thiazol-2-yl)benzo[d]oxazol-2-yl)-3,6-diazabicyclo[3.1.1]heptane-6-carboxylate (10 g, 19.2 mmol) obtained in Synthesis Example 6 was dissolved in dichloromethane (25 mL), and trifluoroacetic acid (18.3 mL, 238.8 mmol) was added, followed by stirring at 40° C. for 2 hours. To the reaction liquid, methanol (30 mL) and dichloromethane (165 mL) were added, and then a 5N aqueous sodium hydroxide solution (100 mL) was added at 30° C. or below followed by stirring. The aqueous layer and the organic layer were separated, and the aqueous layer was extracted again with dichloromethane (10 mL). To the combined organic layers, methanol (30 mL) and water (100 mL) were added followed by stirring. The aqueous layer and the organic layer were separated, and the aqueous layer was extracted again with dichloromethane (10 mL). The combined organic layers were concentrated to 100 mL, and after addition of toluene (50 mL), concentrated to 50 mL. To the liquid concentrate, toluene (100 mL) was added followed by stirring at room temperature for 1 hour and at 55° C. for 1 hour and then by stirring at 0° C. for 1 hour or more. Then, the formed solid was collected by filtration. The obtained solid was washed with toluene (30 mL) having been cooled to 10° C. or below, and dried under reduced pressure. After that, 6.76 g of crude crystals of the title compound were obtained (Percentage yield: 90.9%).

Synthesis Example 8

The crude crystals (20 g) of 1-{[2-(3,6-diazabicyclo[3.1.1]heptan-3-yl)-7-(1,3-thiazol-2-yl)-1,3-benzoxazol-4-yl]oxy}-1,1-difluoro-2-methylpropan-2-ol obtained in Synthesis Example 7 were dissolved in a 85% aqueous ethanol solution (300 mL). The solution was heated to 70° C. After dissolution of the crude crystals was observed, the solution was cooled to 40° C. and filtered. The filtrate was concentrated under reduced pressure to 100 mL, and after addition of ethanol (100 mL), concentrated under reduced pressure to 100 mL followed by the same operation twice. The liquid concentrate was stirred at 0° C. overnight, and a solid was precipitated. The formed solid was collected by filtration, washed with ethanol (40 mL) cooled in advance, and dried under reduced pressure. After that, 17.8 g of recrystallized 1-{[2-(3,6-diazabicyclo[3.1.1]heptan-3-yl)-7-(1,3-thiazol-2-yl)-1,3-benzoxazol-4-yl]oxy}-1,1-difluoro-2-methylpropan-2-ol was obtained (Percentage yield: 89.0%).

$^1$H-NMR (400 MHZ, DMSO-d6) δ ppm: 8.02 (d, J=3.2 Hz, 1H), 7.92 (d, J=3.2 Hz, 1H), 7.76 (d, J=8.7 Hz, 1H), 7.20 (d, J=8.7 Hz, 1H), 5.48 (s, 1H), 3.93-3.80 (m, 4H), 3.69 (d, J=6.0 Hz, 2H), 2.61-2.54 (m, 1H), 1.89 (s, 1H), 1.60 (d, J=9.2 Hz, 1H), 1.41 (s, 6H).

Example 2

[Synthesis Example 1] 4-Benzyloxy-7-bromo-2-ethoxybenzo[d]oxazole

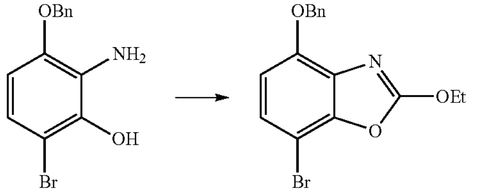 [SMILES: Nc1c(OCc2ccccc2)ccc(Br)c1O ; CCOc1nc2c(OCc3ccccc3)ccc(Br)c2o1]

2-Amino-3-benzyloxy-6-bromophenol (8.83 g, 30.0 mmol) obtained in Synthesis Example 2 of Example 1 was dissolved in toluene (27 mL), and acetic acid (0.86 mL, 15.0 mmol) and tetraethoxymethane (6.34 g, 33.0 mmol) were added followed by heating under reflux for 30 minutes. The reaction liquid was diluted with ethyl acetate, and washed with a 5% aqueous sodium hydrogen carbonate solution and water successively. The obtained organic layer was concentrated, while the solvent was being replaced with 2-propanol to obtain a 72 mL solution, and a solid was precipitated by stirring this solution. After cooling, the formed solid was collected by filtration, washed with 2-propanol, and then dried to obtain 9.84 g of the title compound (Percentage yield: 94.3%).

$^1$H-NMR (400 MHZ, CDCl3) δ ppm: 7.45 (d, J=7.4 Hz, 2H), 7.39-7.27 (m, 3H), 7.12 (d, J=8.7 Hz, 1H), 6.65 (d, J=8.7 Hz, 1H), 5.37 (s, 2H), 4.68 (q, J=7.3 Hz, 2H), 1.51 (t, J=7.3 Hz, 3H).

[Synthesis Example 2] 4-Benzyloxy-2-ethoxy-7-(thiazol-2-yl)benzo[d]oxazole

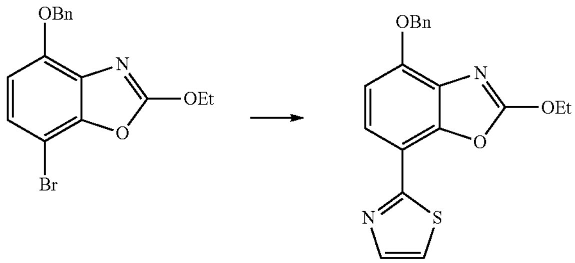 [SMILES: CCOc1nc2c(OCc3ccccc3)ccc(Br)c2o1 ; CCOc1nc2c(OCc3ccccc3)ccc(-c3nccs3)c2o1]

Zinc dust (1.57 g, 24.0 mmol) was suspended in DMF (15 mL), and chlorotrimethylsilane (0.25 mL, 2.0 mmol) was added, followed by stirring at 50° C. for 1 hour. The reaction liquid was heated to 60° C., and 2-bromothiazole (1.8 mL, 20.3 mmol) was added followed by stirring. Then, 4-benzyloxy-7-bromo-2-ethoxybenzo[d]oxazole (3.48 g, 10.0 mmol) obtained in Synthesis Example 1, [1,1'-bis(diphenylphosphino)ferrocene] dichloropalladium(II) dichloromethane adduct (0.24 g, 0.29 mmol), and DMF (10 mL) were added followed by stirring at 80° C. or above for 1 hour and by cooling. To the reaction liquid, toluene (35 mL), DMF (18 mL), and 20-fold diluted sulfuric acid (18 mL) were added, followed by stirring for 1 hour. Then, the aqueous layer was removed. To the obtained organic layer, DMF (18 mL) and 20-fold diluted sulfuric acid (18 mL) were added followed by stirring, and then the aqueous layer was removed. The obtained organic layer was washed with water. The same operation was conducted again, and the same amount of an organic layer was obtained. The obtained organic layers were mixed, and concentrated, while the solvent was being replaced with 2-propanol to obtain a 70 mL solution. A solid was precipitated by stirring the solution. After cooling, the solid was collected by filtration, washed with 2-propanol, and dried to obtain 6.06 g of the title compound (Percentage yield: 86.0%).

$^1$H-NMR (400 MHz, $CDCl_3$) δ ppm: 7.91 (d, J=3.2 Hz, 1H), 7.84 (d, J=9.2 Hz, 1H), 7.49 (d, J=7.4 Hz, 2H), 7.40-7.30 (m, 4H), 6.86 (d, J=9.2 Hz, 1H), 5.45 (s, 2H), 4.72 (q, J=6.8 Hz, 2H), 1.55 (t, J=6.8 Hz, 3H).

[Synthesis Example 3] tert-Butyl 3-(4-Benzyloxy-7-(thiazol-2-yl)benzo[d]oxazol-2-yl)-3,6-diazabicyclo[3.1.1]heptane-6-carboxylate

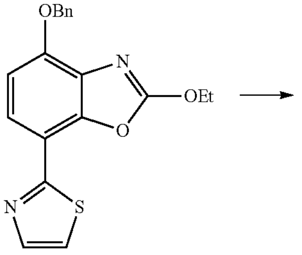

-continued

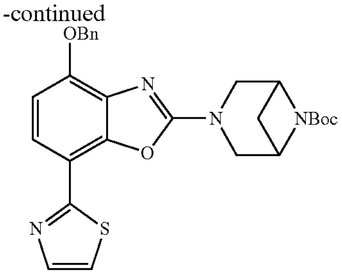

4-Benzyloxy-2-ethoxy-7-(thiazol-2-yl)benzo[d]oxazole (3.0 g, 8.5 mmol) obtained in Synthesis Example 2 was dissolved in toluene (12 mL), and tert-butyl 3,6-diazabicyclo [3.1.1]heptane-6-carboxylate (1.86 g, 9.4 mmol) and acetic acid (0.25 mL, 4.4 mmol) were added, followed by heating under reflux for 1 hour. The reaction liquid was diluted with toluene, and washed with a 5% aqueous sodium hydrogen carbonate solution and water successively. The obtained organic layer was concentrated, while the solvent was being replaced with 2-propanol to obtain a 30 mL solution. A solid was precipitated by stirring this solution. After cooling, the solid was collected by filtration, washed with 2-propanol, and then dried to obtain 3.97 g of the title compound (Percentage yield: 92.5%). The $^{1}$H-NMR was identical to that of the compound obtained Synthesis Example 4 of Example 1.

Example 3

[Synthesis Example 1]5,7-Dibromo-2-ethoxybenzo [d]oxazol-4-ol

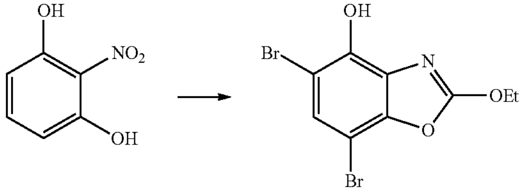 [SMILES: O=[N+]([O-])c1c(O)cccc1O ; CCOc1nc2c(O)c(Br)cc(Br)c2o1]

2-Nitroresorcinol (5.0 g, 32.235 mmol) was dissolved in ethyl acetate (50 mL), and 10% Pd—C (PEtype) (0.25 g) was added followed by vigorous stirring under a hydrogen atmosphere at room temperature for 1.5 hours to obtain a reaction liquid containing 2-aminoresorcinol. The reaction liquid was filtered through Celite, and the filter cake was washed with ethyl acetate (30 mL in several portions), and the filtrate was concentrated under reduced pressure to 50 mL. To this solution, ethyl acetate (25 mL), acetic acid (0.92 mL, 16.060 mmol), and tetraethoxymethane (10.1 mL, 48.330 mmol) were added under a nitrogen atmosphere, followed by stirring at 85° C. for 1 hour to obtain a reaction liquid containing 2-ethoxybenzo[d]oxazol-4-ol. The reaction liquid was cooled, then washed with a 5% aqueous sodium hydrogen carbonate solution (50 mL) and water (50 mL) successively, and concentrated under reduced pressure to 50 mL. To the obtained solution, ethyl acetate (50 mL) was added, and N-bromosuccinimide (12.05 g, 67.770 mmol) was added portionwise under ice-cooling. The temperature was raised to room temperature followed by stirring for 1 hour to obtain a reaction liquid containing the title compound. To the reaction liquid, ethyl acetate (50 mL) was added, followed by washing with a 20% aqueous sodium hydrogen sulfite solution (50 mL) and twice with 5% aqueous sodium chloride (50 mL) successively. The obtained organic layer was concentrated under reduced pressure to 50 mL, and addition of ethanol (50 mL) and concentration under reduced pressure to 50 mL were repeated twice. To the solution, water (100 mL) was added dropwise to precipitate a solid, followed by maturation under ice-cooling for 1 hour. The obtained solid was collected by filtration, washed with ethanol/water=1/3 (40 mL in several portions), and dried under reduced pressure to obtain 8.73 g of the title compound (Percentage yield: 80.4%).

$^{1}$H-NMR (400 MHZ, CDCl3) δ ppm: 7.45 (s, 1H), 4.65 (q, J=6.9 Hz, 2H), 1.52 (t, J=6.9 Hz, 3H). [Synthesis Example 2] tert-Butyl 3-(5,7-Dibromo-4-hydroxybenzo[d] oxazol-2-yl)-3,6-diazabicyclo[3.1.1]heptane-6-carboxylate

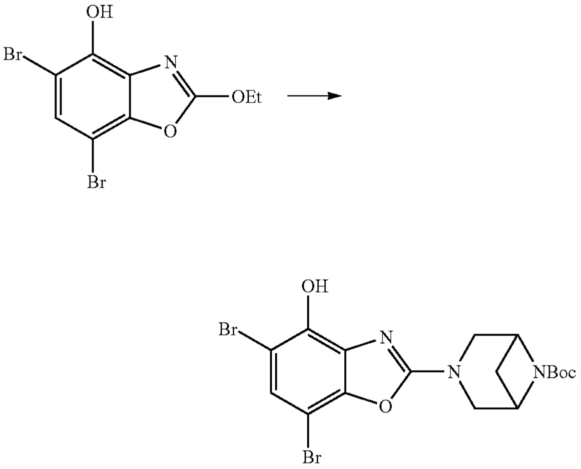

5,7-Dibromo-2-ethoxybenzo[d]oxazol-4-ol (7.00 g, 20.773 mmol) obtained in Synthesis Example 1 and tert-butyl 3,6-diazabicyclo[3.1.1]heptane-6-carboxylate (4.94 g, 24.916 mmol) were dissolved in toluene (70 mL) followed by heating to 125° C. and by stirring for 2 hours. The reaction liquid was cooled, and then concentrated under reduced pressure to a 35 mL solution. Then, n-hexane (175 mL) was added dropwise to precipitate a solid followed by maturation under ice-cooling for 1 hour. The obtained solid was collected by filtration, washed with toluene/n-hexane=1/4 (35 mL in several portions), and dried under reduced pressure. The obtained solid was dissolved in THE (90 mL), and concentrated under reduced pressure to 48 mL. Addition of ethyl acetate (63 mL) and concentration under reduced pressure to 48 mL were repeated three times. The obtained solution was stirred at 60° C. for 30 minutes, and the temperature was lowered to room temperature, followed by maturation for 1 hour under ice cooling. The obtained solid was collected by filtration, and washed with cold ethyl acetate (18 mL in several portions), and then dried under reduced pressure to obtain 7.77 g of the title compound (Percentage yield: 84.8%).

$^{1}$H-NMR (400 MHZ, DMSO-d6) δ: 10.65 (s, 1H), 7.34 (s, 1H), 4.02-4.26 (m, 4H), 3.66 (br d, J=11.0 Hz, 2H), 2.53-2.63 (m, 1H), 1.57 (d, J=9.2 Hz, 1H), 1.29 (s, 9H).

[Synthesis Example 3] tert-Butyl 3-(5-Bromo-4-hydroxy-7-(thiazol-2-yl)benzo[d]oxazol-2-yl)-3,6-diazabicyclo[3.1.1]heptane-6-carboxylate

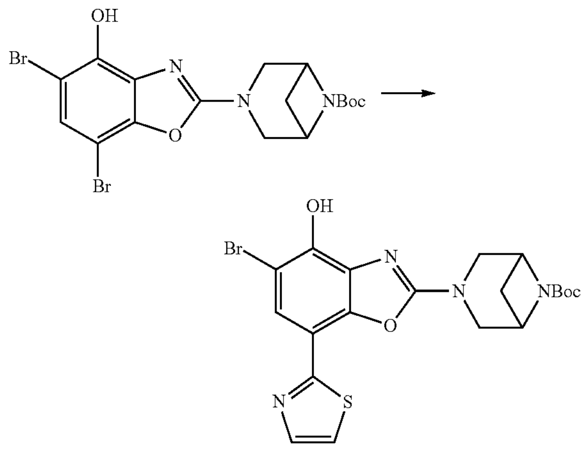

Anhydrous lithium chloride (2.22 g, 51.11 mmol) and zinc dust (5.01 g, 76.65 mmol) were suspended in THF (10 mL), and chlorotrimethylsilane (0.45 mL, 3.58 mmol) was added under a nitrogen atmosphere, followed by vigorous stirring at 60° C. for 2 hours. 2-Bromothiazole (4.53 mL, 51.11 mmol) was slowly added dropwise, and a solution of tert-butyl 3-(5,7-dibromo-4-hydroxybenzo[d]oxazol-2-yl)-3,6-diazabicyclo[3.1.1]heptane-6-carboxylate (5.00 g, 10.22 mmol) obtained in Synthesis Example 2 in DMF (15 mL), palladium(II) acetate (0.229 g, 1.022 mmol), and tri(p-tolyl) phosphine (1.24 g, 4.09 mmol) were rapidly added by using DMF (15 mL). Then, the temperature was raised to 85° C. followed by stirring for 2.5 hours. The reaction liquid was cooled with ice, and chloroform (50 mL), toluene (25 mL), DMF (50 mL), and a 1.8 M aqueous sulfuric acid solution (50 mL) were added followed by stirring for 30 minutes. After standing, the aqueous layer was separated, and the obtained organic layer was washed with a mixture solution of DMF (50 mL) and a 1.8 M aqueous sulfuric acid solution (50 mL). The obtained aqueous layer was combined with the previous aqueous layer, and extracted again with a mixture solution of chloroform (40 mL) and toluene (20 mL). The obtained organic layer was combined with the previous organic layer, and washed twice with water (100 mL). To the organic layer, activated carbon (0.5 g) and a 20% aqueous sodium hydrogen sulfite solution (100 mL) were added, followed by stirring at 60° C. for 1 hour. After cooling, filtration was conducted through Celite, the filter cake was washed with chloroform, and the filtrate was subjected to liquid-liquid separation. The obtained organic layer was washed twice with water (100 mL), and then the organic layer was concentrated under reduced pressure to 30 mL. Addition of toluene (100 mL) to the obtained solution and concentration under reduced pressure to 30 mL were repeated twice. Subsequently, addition of ethanol (100 mL) and concentration under reduced pressure to 30 mL were repeated twice. The obtained solution was cooled with ice for crystallization and maturation, and the crystals were collected by filtration, and dried under reduced pressure to obtain 4.88 g of the title compound (Percentage yield: 96.8%).

$^1$H-NMR (400 MHZ, CDC13) ¿: 8.10 (s, 1H), 7.92 (d, J=3.2 Hz, 1H), 7.43 (d, J=3.2 Hz, 1H), 4.32 (br m, 4H), 3.78 (br d, J=11.9 Hz, 2H), 2.66-2.83 (m, 1H), 1.57 (d, J=9.2 Hz, 1H), 1.38 (s, 9H).

[Synthesis Example 4] tert-Butyl 3-(4-Hydroxy-7-(thiazol-2-yl)benzo[d]oxazol-2-yl)-3,6-diazabicyclo[3.1.1]heptane-6-carboxylate

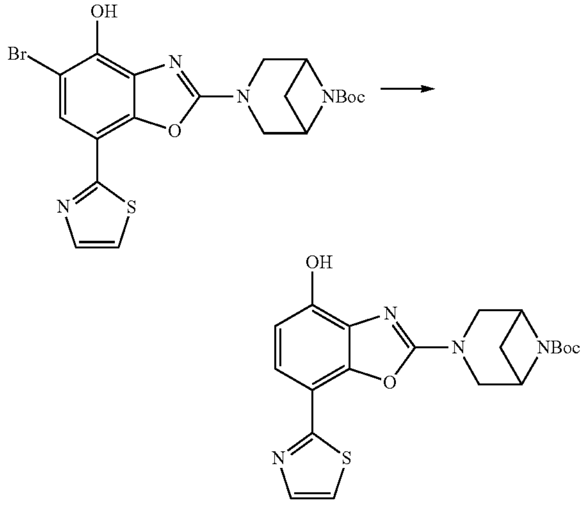

tert-Butyl 3-(5-bromo-4-hydroxy-7-(thiazol-2-yl)benzo[d]oxazol-2-yl)-3,6-diazabicyclo[3.1.1]heptane-6-carboxylate (0.469 g, 0.951 mmol) obtained in Synthesis Example 3, ammonium formate (1.50 g, 23.79 mmol), and zinc dust (1.554 g, 23.77 mmol) were suspended in ethanol (7 mL), and refluxed under a nitrogen atmosphere for 2 hours. The suspension was cooled, and then ethyl acetate (4.7 mL) was added followed by stirring. Then, filtration was conducted through Celite, and the filter cake was washed with ethyl acetate (9.4 mL in several portions). The filtrate was washed with a 5% aqueous potassium hydrogen sulfate solution (9.4 mL) and a 5% aqueous sodium chloride (9.4 mL) successively. The obtained organic layer was concentrated under reduced pressure to 4.7 and addition mL, of acetonitrile (9.4 mL) and concentration under reduced pressure to 4.7 mL were repeated twice. The obtained solution was stirred at room temperature for 2 hours, and then cooled with ice for 1 hour for crystallization and maturation to obtain 397 mg (Percentage yield: 91.7%) of a monoacetonitrile solvate of the title compound. The $^1$H-NMR was identical to that of the compound obtained in Synthesis Example 5 of Example 1.

INDUSTRIAL APPLICABILITY

According to the present invention, it is possible to provide a novel method for producing 1-{[2-(3,6-diazabicyclo[3.1.1]heptan-3-yl)-7-(thiazol-2-yl)benzo[d]oxazol-4-yl]oxy}-1,1-difluoro-2-methylpropan-2-ol (compound (1)) or a salt thereof, the method being excellent in safety and handleability and being suitable for industrial production. Moreover, according to the present invention, it is also possible to provide a 2-alkoxybenzo[d]oxazole derivative (compound (2)) or a salt thereof as a material usable in the method for producing a compound (1) or a salt thereof, as well as a production method thereof.

The compound (2) according to the present invention can be produced by a method which does not require a reagent that is highly toxic and difficult to handle or a high-risk operation and further which does not involve generation of a toxic substance during a reaction. Moreover, the production of the compound (1) or a salt thereof by using the compound (2) does not require a reagent that is highly toxic and difficult to handle or a high-risk operation, either. In addition, according to the present invention, it is also possible to reduce the number of steps in composition with the already-existing production method, and it is also possible to obtain a compound (1) or a salt thereof in a high percentage yield comparable to those achieved by the already-existing production method. Accordingly, the method for producing a compound (1) or a salt thereof and the method for producing a compound (2) or a salt thereof used in the method of the present invention are extremely useful industrially.

The invention claimed is:

1. A method for producing a compound represented by formula (1):

(1)

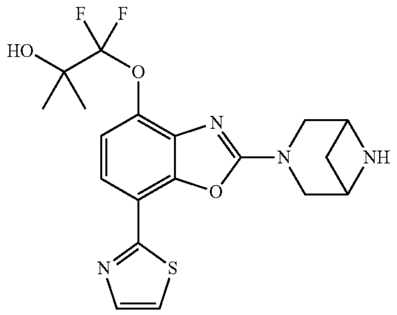

or a salt thereof, comprising:

a step B of producing a compound represented by formula (3):

(3)

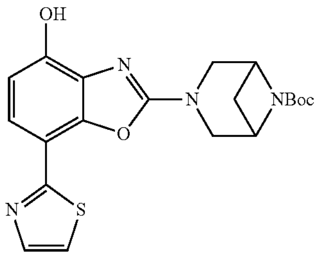

[in the formula (3), Boc represents a tert-butoxycarbonyl group]

or a salt thereof by using a compound represented by formula (2):

(2)

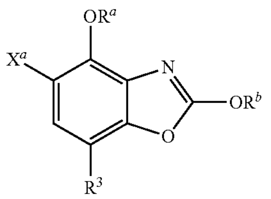

[in the formula (2), $R^a$ represents a hydrogen atom or an optionally substituted arylmethyl group, $R^b$ represents an optionally substituted alkyl or cyclic alkyl group, $R^3$ represents a hydrogen atom, a halogen atom, or a thiazol-2-yl group, and $X^a$ represents a hydrogen atom or a halogen atom]

or a salt thereof; and a step C of producing a compound represented by the formula (1) or a salt thereof by using the compound represented by the formula (3) or the salt thereof.

2. The production method according to claim 1, wherein the step B is a step of substituting $OR^b$ of a compound (2-1) represented by the formula (2), where $R^a$ is an optionally substituted arylmethyl group, $R^b$ is an optionally substituted alkyl group, $R^3$ is a halogen atom, and $X^a$ is a hydrogen atom, with tert-butyl 3,6-diazabicyclo[3.1.1]heptane-6-carboxylate, to produce a compound represented by formula (4):

(4)

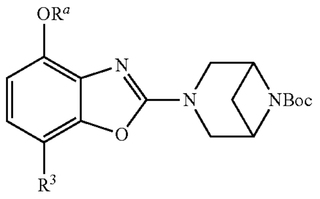

[in the formula (4), $R^a$ is an optionally substituted arylmethyl group, $R^3$ is a halogen atom, and Boc is a tert-butoxycarbonyl group], introducing a thiazol-2-yl group to the compound represented by the formula (4) by a cross-coupling reaction in the presence of a metal catalyst, to produce a compound represented by formula (5):

(5)

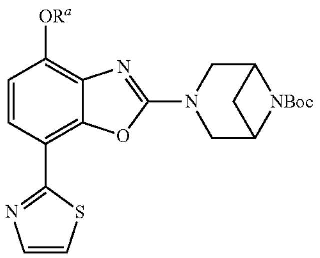

[in the formula (5), $R^a$ is an optionally substituted arylmethyl group, and Boc is a tert-butoxycarbonyl group], and reacting the compound represented by the formula (5) with an organic acid, to produce the compound represented by the formula (3) or the salt thereof.

3. The production method according to claim 1, wherein the step B is a step of introducing a thiazol-2-yl group to a compound (2-1) represented by the formula (2), where $R^a$ is an optionally substituted arylmethyl group, $R^b$ is an optionally substituted alkyl group, $R^3$ is a halogen atom, and $X^a$ is a hydrogen atom, by a cross-coupling reaction in the presence of a metal catalyst, to produce a compound (2-11) represented by the formula (2), where $R^a$ is an optionally substituted arylmethyl group, $R^b$ is an optionally substituted alkyl group, $R^3$ is a thiazol-2-yl group, and $X^a$ is a hydrogen atom, substituting $OR^b$ of the compound (2-11) with tert-butyl 3,6-diazabicyclo[3.1.1]heptane-6-carboxylate, to produce a compound represented by formula (5):

(5)

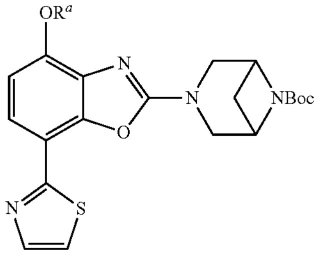

[in the formula (5), $R^a$ is an optionally substituted arylmethyl group, and Boc is a tert-butoxycarbonyl group], and reacting the compound represented by the formula (5) with an organic acid, to produce the compound represented by the formula (3) or the salt thereof.

4. The production method according to claim 1, wherein the step B is a step of reacting a compound (2-2) represented by the formula (2), where $R^a$ is a hydrogen atom, $R^b$ is an optionally substituted alkyl group, $R^3$ is a hydrogen atom, and $X^a$ is a hydrogen atom, with a brominating agent, to produce a compound (2-21) represented by the formula (2), where $R^a$ is a hydrogen atom, $R^b$ is an optionally substituted alkyl group, $R^3$ is a bromine atom, and $X^a$ is a bromine atom, substituting $OR^b$ of the compound (2-21) with tert-butyl 3,6-diazabicyclo[3.1.1]heptane-6-carboxylate, to produce a compound represented by formula (8):

(8)

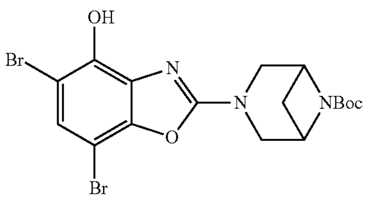

[in the formula (8), Boc is a tert-butoxycarbonyl group], introducing a thiazol-2-yl group to the compound represented by the formula (8) by a cross-coupling reaction in the presence of a metal catalyst, to produce a compound represented by formula (9):

(9)

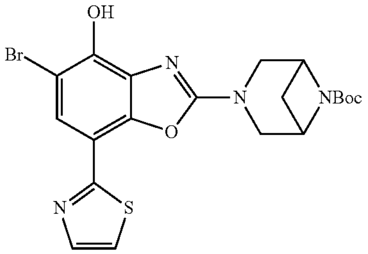

[in the formula (9), Boc is a tert-butoxycarbonyl group], and reacting the compound represented by the formula (9) with a metal, to produce the compound represented by the formula (3) or the salt thereof.

5. The production method according to claim 1, comprising a step A of producing the compound represented by the formula (2) or the salt thereof by using a compound represented by formula (10):

(10)

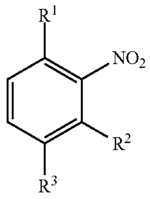

[in the formula (10), $R^1$ represents a hydroxy group or a halogen atom or an arylmethyloxy group, $R^2$ represents a hydroxy group or a halogen atom, $R^3$ represents a hydrogen atom, a halogen atom, or a thiazol-2-yl group], or a salt thereof.

6. The production method according to claim 5, wherein the step A is a step of reacting a compound (10-1) represented by the formula (10), where $R^1$ is a halogen atom, $R^2$ is a halogen atom, and $R^3$ is a hydrogen atom, with benzyl alcohol, to produce a compound represented by formula (10-11):

(10-11)

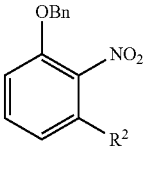

[in the formula (10-11), $R^2$ is a halogen atom, and Bn is a benzyl group], reacting the compound represented by the formula (10-11) with a brominating agent, to produce a compound represented by formula (10-12):

(10-12)

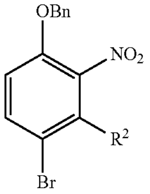

[in the formula (10-12), $R^2$ is a halogen atom, and Bn is a benzyl group], reacting the compound represented by the formula (10-12) with an aqueous alkaline solution, to produce a compound represented by formula (10-13):

(10-13)

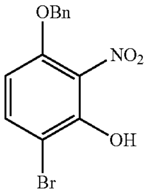

[in the formula (10-13), Bn is a benzyl group], reacting the compound represented by the formula (10-13) with a reducing agent, to produce a compound represented by formula (14):

(14)

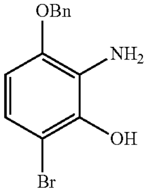

[in the formula (14), Bn is a benzyl group], and reacting the compound represented by the formula (14) with a tetraalkoxymethane in the presence of an acid catalyst, to produce the compound represented by the formula (2) or the salt thereof.

7. The production method according to claim 5, wherein the step A is a step of reducing a compound (10-2) represented by the formula (10), where $R^1$ is a hydroxy group, $R^2$ is a hydroxy group, and $R^3$ is a hydrogen atom, followed by a reaction with a tetraalkoxymethane in the presence of an acid catalyst and then by a reaction with a brominating agent, to produce the compound represented by the formula (2) or the salt thereof.

8. A compound represented by formula (15):

(15)

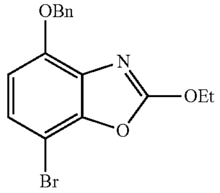

[in the formula (15), Bn is a benzyl group, and Et is an ethyl group]

or a salt thereof.

9. A compound represented by formula (6):

(6)

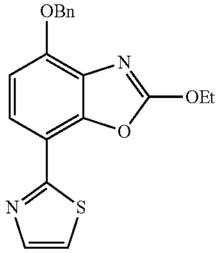

[in the formula (6), Bn is a benzyl group, and Et is an ethyl group]

or a salt thereof.

10. A compound represented by formula (7):

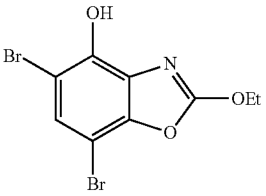 [SMILES: CCOc1nc2c(O)c(Br)cc(Br)c2o1]

[in the formula (7), Et is an ethyl group]

or a salt thereof.

11. A compound represented by formula (8):

(8)

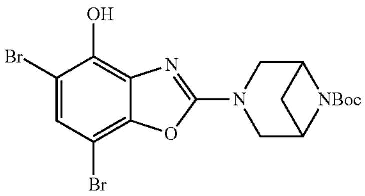

[in the formula (8), Boc is a tert-butoxycarbonyl group]

or a salt thereof.

* * * * *